(12) United States Patent
Berg et al.

(10) Patent No.: US 6,508,252 B1
(45) Date of Patent: Jan. 21, 2003

(54) MEDICAL GRAFTING METHODS AND APPARATUS

(75) Inventors: Todd Allen Berg, Plymouth; Daniel J. Sullivan, Medina; William J. Swanson, St. Paul; Paul J. Hindrichs, Plymouth, all of MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 0 days.

(21) Appl. No.: 09/430,506

(22) Filed: Oct. 29, 1999

Related U.S. Application Data

(60) Provisional application No. 60/107,294, filed on Nov. 6, 1998.

(51) Int. Cl.$^7$ ............................................. A61B 19/00
(52) U.S. Cl. ..................... 128/898; 606/153; 606/151; 606/194; 604/158; 623/1.23; 623/1.36; 623/12
(58) Field of Search ................ 623/1.23, 1.36; 128/898; 604/8, 158, 159, 164; 606/8, 153, 158, 167, 170, 191, 151, 194–195, 185

(56) References Cited

U.S. PATENT DOCUMENTS

| | | | |
|---|---|---|---|
| 3,796,211 A | 3/1974 | Kohl | 128/2 B |
| 3,867,945 A | 2/1975 | Long | 128/349 R |
| 3,903,892 A | 9/1975 | Komiya | 128/303.15 |
| 4,214,587 A | 7/1980 | Sakura, Jr. | 128/334 R |
| 4,418,693 A | 12/1983 | LeVeen et al. | 128/303 R |
| 4,459,252 A | 7/1984 | MacGregor | 264/46.9 |
| 4,470,415 A | 9/1984 | Wozniak | 128/334 R |
| 4,503,569 A | 3/1985 | Dotter | 3/1.4 |
| 4,545,390 A | 10/1985 | Leary | 128/772 |
| 4,592,754 A | 6/1986 | Gupte et al. | 623/1 |
| 4,605,406 A | 8/1986 | Cahalan et al. | 623/1 |
| 4,617,932 A | 10/1986 | Kornberg | 128/334 R |
| 4,629,458 A | 12/1986 | Pinchuk | 623/1 |
| 4,632,842 A | 12/1986 | Karwoski et al. | 427/2 |
| 4,651,733 A | 3/1987 | Mobin-Uddin | 128/303 R |
| 4,665,906 A | 5/1987 | Jervis | 128/92 YN |

(List continued on next page.)

FOREIGN PATENT DOCUMENTS

| | | | |
|---|---|---|---|
| AU | 670239 | 1/1994 | A61F/2/06 |
| DE | 4404806 C1 | 2/1995 | A61B/17/22 |
| EP | 539237 A1 | 4/1993 | A61F/2/06 |
| EP | 637454 A1 | 2/1995 | A61M/5/10 |
| EP | 680734 A2 | 8/1995 | A61F/2/06 |
| EP | 684022 A2 | 11/1995 | A61F/2/06 |
| EP | 701800 A1 | 3/1996 | A61F/2/06 |
| EP | 712614 A1 | 5/1996 | A61F/2/06 |
| EP | 723786 A1 | 7/1996 | A61M/25/00 |
| EP | 732087 A1 | 9/1996 | A61F/2/06 |
| EP | 737453 A2 | 10/1996 | A61F/2/06 |
| EP | 807412 A1 | 11/1997 | A61B/17/32 |
| GB | 2269104 A | 2/1994 | A61F/2/06 |
| WO | WO 89/08433 | 9/1989 | A61F/2/04 |
| WO | WO 93/00868 | 1/1993 | A61F/2/06 |
| WO | WO 93/20757 | 10/1993 | A61B/17/11 |
| WO | WO 94/01056 | 1/1994 | A61F/2/04 |

(List continued on next page.)

*Primary Examiner*—David J. Isabella
*Assistant Examiner*—Urmi Chattopadhyay

(57) ABSTRACT

Methods and apparatus for delivering and installing a new length of tubing between two sections of a patient's existing body organ tubing and at least partly outside of that existing structure. For example, the new length of tubing may be for the purpose of providing the patient with a coronary bypass. The new tubing may be an artificial graft, a natural graft (harvested elsewhere from the patient), or both. The new tubing is installed at the operative site primarily by providing at least one graft location with instrumentation inserted through the patient's existing tubular body organ structure. Assistance in installing the new tubing may be provided by minimally invasive surgical access openings in the patient's chest. The tubing may be delivered through the patient's existing tubular body structure or, alternatively, through the surgical access openings.

18 Claims, 31 Drawing Sheets

U.S. PATENT DOCUMENTS

| | | | |
|---|---|---|---|
| 4,705,517 A | 11/1987 | DiPisa, Jr. | 623/12 |
| 4,718,907 A | 1/1988 | Karwoski et al. | 623/12 |
| 4,733,665 A | 3/1988 | Palmaz | 128/343 |
| 4,738,740 A | 4/1988 | Pinchuk et al. | 156/167 |
| 4,743,252 A | 5/1988 | Martin, Jr. et al. | 623/1 |
| 4,748,984 A | 6/1988 | Patel | 128/658 |
| 4,787,899 A | 11/1988 | Lazarus | 623/1 |
| 4,795,458 A | 1/1989 | Regan | 623/1 |
| 4,798,606 A | 1/1989 | Pinchuk | 623/1 |
| 4,892,539 A | 1/1990 | Koch | 623/1 |
| 4,911,163 A | 3/1990 | Fina | 606/127 |
| 4,969,890 A | 11/1990 | Sugita et al. | 606/192 |
| 5,035,702 A | 7/1991 | Taheri | 606/153 |
| 5,037,377 A | 8/1991 | Alonso | 600/36 |
| 5,061,245 A | 10/1991 | Waldvogel | 604/170 |
| 5,061,275 A | 10/1991 | Wallsten et al. | 623/1 |
| 5,084,065 A | 1/1992 | Weldon et al. | 623/1 |
| 5,104,399 A | 4/1992 | Lazarus | 623/1 |
| 5,116,360 A | 5/1992 | Pinchuk et al. | 623/1 |
| 5,122,154 A | 6/1992 | Rhodes | 606/198 |
| 5,122,156 A | 6/1992 | Granger et al. | 606/219 |
| 5,135,467 A | 8/1992 | Citron | 600/16 |
| 5,147,370 A | 9/1992 | McNamara et al. | 606/108 |
| 5,163,951 A | 11/1992 | Pinchuk et al. | 623/1 |
| 5,171,233 A | 12/1992 | Amplatz et al. | 604/281 |
| 5,201,901 A | 4/1993 | Harada et al. | 606/198 |
| 5,207,695 A | 5/1993 | Trout, III | 606/153 |
| 5,209,731 A | 5/1993 | Sterman et al. | 604/97 |
| 5,211,658 A | 5/1993 | Clouse | 623/1 |
| 5,211,683 A | 5/1993 | Maginot | 128/898 |
| 5,226,429 A | 7/1993 | Kuzmak | 128/898 |
| 5,234,447 A | 8/1993 | Kaster et al. | 606/153 |
| 5,256,150 A | 10/1993 | Quiachon et al. | 604/171 |
| 5,275,622 A | 1/1994 | Lazarus et al. | 623/1 |
| 5,287,861 A | 2/1994 | Wilk | 128/898 |
| 5,297,564 A | 3/1994 | Love | 128/898 |
| 5,304,220 A | 4/1994 | Maginot | 623/1 |
| 5,306,240 A | 4/1994 | Berry | 604/51 |
| 5,316,023 A | 5/1994 | Palmaz et al. | 128/898 |
| 5,330,500 A | 7/1994 | Song | 606/198 |
| 5,334,217 A | 8/1994 | Das | 606/213 |
| 5,354,309 A | 10/1994 | Schnepp-Pesch et al. | 606/198 |
| 5,354,336 A | 10/1994 | Kelman et al. | 623/6 |
| 5,360,443 A | 11/1994 | Barone et al. | 623/1 |
| 5,366,441 A | 11/1994 | Crawford | 604/53 |
| 5,366,504 A | 11/1994 | Anderson et al. | 623/11 |
| 5,387,235 A | 2/1995 | Chuter | 623/1 |
| 5,395,349 A | 3/1995 | Quiachon et al. | 604/248 |
| 5,397,345 A | 3/1995 | Lazarus | 623/1 |
| 5,397,355 A | 3/1995 | Marin et al. | 623/12 |
| 5,409,019 A | 4/1995 | Wilk | 128/898 |
| 5,419,324 A | 5/1995 | Dillow | 128/653.1 |
| 5,425,765 A | 6/1995 | Tiefenbrun et al. | 623/12 |
| 5,429,144 A | 7/1995 | Wilk | 128/898 |
| 5,433,727 A | 7/1995 | Sideris | 606/213 |
| 5,437,288 A | 8/1995 | Schwartz et al. | 128/772 |
| 5,443,497 A | 8/1995 | Venbrux | 623/1 |
| 5,443,499 A | 8/1995 | Schmitt | 623/1 |
| 5,452,733 A | 9/1995 | Sterman et al. | 128/898 |
| 5,456,712 A | 10/1995 | Maginot | 623/1 |
| 5,480,423 A | 1/1996 | Ravenscroft et al. | 623/1 |
| 5,484,418 A | 1/1996 | Quiachon et al. | 604/167 |
| 5,488,958 A | 2/1996 | Topel et al. | 128/754 |
| 5,489,295 A | 2/1996 | Piplani et al. | 623/1 |
| 5,496,365 A | 3/1996 | Sgro | 623/1 |
| 5,507,769 A | 4/1996 | Marin et al. | 606/198 |
| 5,509,931 A | 4/1996 | Schmitt | 623/1 |
| 5,522,834 A | 6/1996 | Fonger et al. | 606/194 |
| 5,522,880 A | 6/1996 | Barone et al. | 623/1 |
| 5,522,882 A | 6/1996 | Gaterud et al. | 623/1 |
| 5,542,944 A | 8/1996 | Bhatta | 606/33 |
| 5,545,214 A | 8/1996 | Stevens | 623/2 |
| 5,549,663 A | 8/1996 | Cottone, Jr. | 623/1 |
| 5,554,152 A | 9/1996 | Aita et al. | 606/7 |
| 5,562,725 A | 10/1996 | Schmitt et al. | 623/1 |
| 5,562,728 A | 10/1996 | Lazarus et al. | 623/1 |
| 5,571,167 A | 11/1996 | Maginot | 623/1 |
| 5,571,172 A | 11/1996 | Chin | 623/1 |
| 5,571,215 A | 11/1996 | Sterman et al. | 623/66 |
| 5,584,875 A | 12/1996 | Duhamel et al. | 623/1 |
| 5,628,786 A | 5/1997 | Banas et al. | 623/1 |
| 5,628,788 A | 5/1997 | Pinchuk | 623/1 |
| 5,632,772 A | 5/1997 | Alcime et al. | 623/1 |
| 5,653,747 A | 8/1997 | Dereume | 623/1 |
| 5,676,670 A | 10/1997 | Kim | 606/108 |
| 5,693,083 A | 12/1997 | Baker et al. | 623/1 |
| 5,695,504 A | 12/1997 | Gifford, III et al. | 606/153 |
| 5,702,412 A | 12/1997 | Popov et al. | 606/159 |
| 5,707,380 A | 1/1998 | Hinchliffe et al. | 606/153 |
| 5,755,778 A | 5/1998 | Kleshinski | 623/1 |
| 5,797,920 A | 8/1998 | Kim | 606/108 |
| 5,830,222 A | 11/1998 | Makower | 606/159 |
| 5,843,164 A | 12/1998 | Frantzen et al. | 623/1 |
| 5,843,170 A | 12/1998 | Ahn | 623/1 |
| 5,843,175 A | 12/1998 | Frantzen | 623/1 |
| 5,922,022 A | 7/1999 | Nash et al. | 623/1 |
| 5,941,908 A | 8/1999 | Goldsteen et al. | 623/1 |
| 5,972,017 A | 10/1999 | Berg et al. | 606/198 |
| 5,976,178 A | 11/1999 | Goldsteen et al. | 623/1 |
| 6,001,124 A | 12/1999 | Bachinski | 623/1 |
| 6,026,814 A | 2/2000 | LaFontaine et al. | 128/898 |
| 6,035,856 A | 3/2000 | LaFontaine et al. | 128/898 |

FOREIGN PATENT DOCUMENTS

| | | | |
|---|---|---|---|
| WO | WO 94/06372 | 3/1994 | A61F/2/04 |
| WO | WO 95/17127 | 6/1995 | A61B/17/11 |
| WO | WO 95/21592 | 8/1995 | A61F/2/06 |
| WO | WO 96/01591 | 1/1996 | A61B/17/22 |
| WO | WO 96/01599 | 1/1996 | A61F/2/06 |
| WO | WO 96/14808 | 5/1996 | A61F/2/02 |
| WO | WO 96/18361 | 6/1996 | A61F/2/06 |
| WO | WO 96/22745 | 8/1996 | A61F/2/06 |
| WO | WO 96/25897 | 8/1996 | A61F/2/06 |
| WO | WO 97/12555 | 4/1997 | A61B/17/11 |
| WO | WO 97/13463 | 4/1997 | A61B/17/00 |
| WO | WO 97/13471 | 4/1997 | A61B/19/00 |
| WO | WO 97/27893 | 8/1997 | A61M/19/00 |
| WO | WO 97/27897 | 8/1997 | A61M/29/00 |
| WO | WO 97/27898 | 8/1997 | A61M/29/00 |
| WO | WO 98/02099 | 1/1998 | A61B/17/00 |
| WO | WO 98/08456 | 3/1998 | A61B/19/00 |
| WO | WO 98/16161 | 4/1998 | A61B/17/36 |
| WO | WO 98/19618 | 5/1998 | A61B/19/00 |
| WO | WO 98/19629 | 5/1998 | A61F/2/06 |
| WO | WO 98/19634 | 5/1998 | A61F/2/06 |
| WO | WO 98/19635 | 5/1998 | A61F/2/06 |
| WO | WO 98/38939 | 9/1998 | A61B/19/00 |
| WO | WO 98/38941 | 9/1998 | A61B/19/00 |
| WO | WO 98/42262 | 10/1998 | A61B/17/04 |

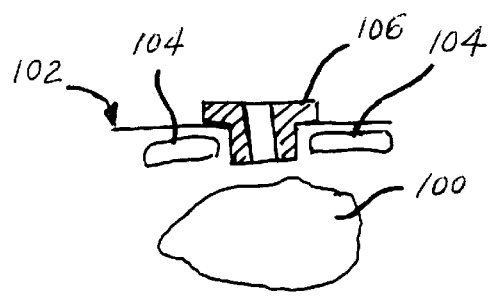
FIG. 2-a
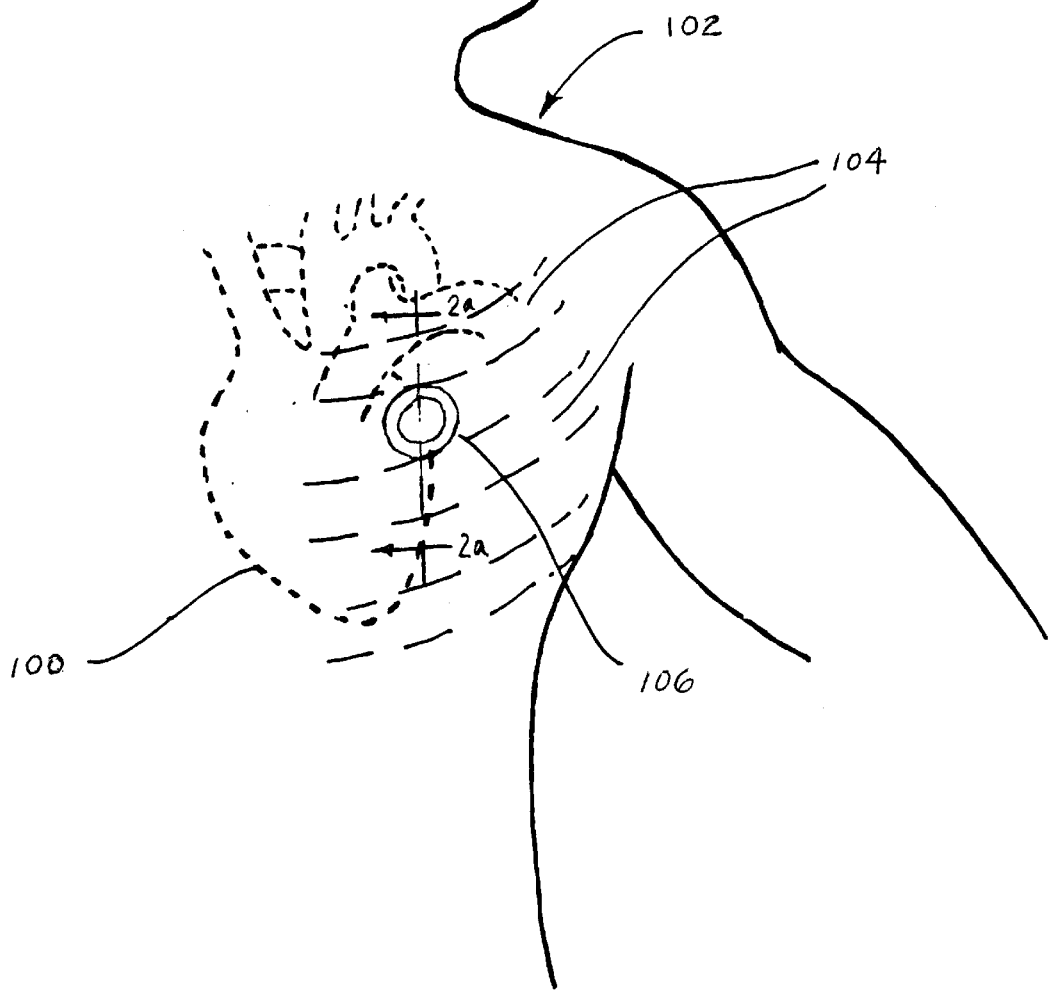
FIG. 2

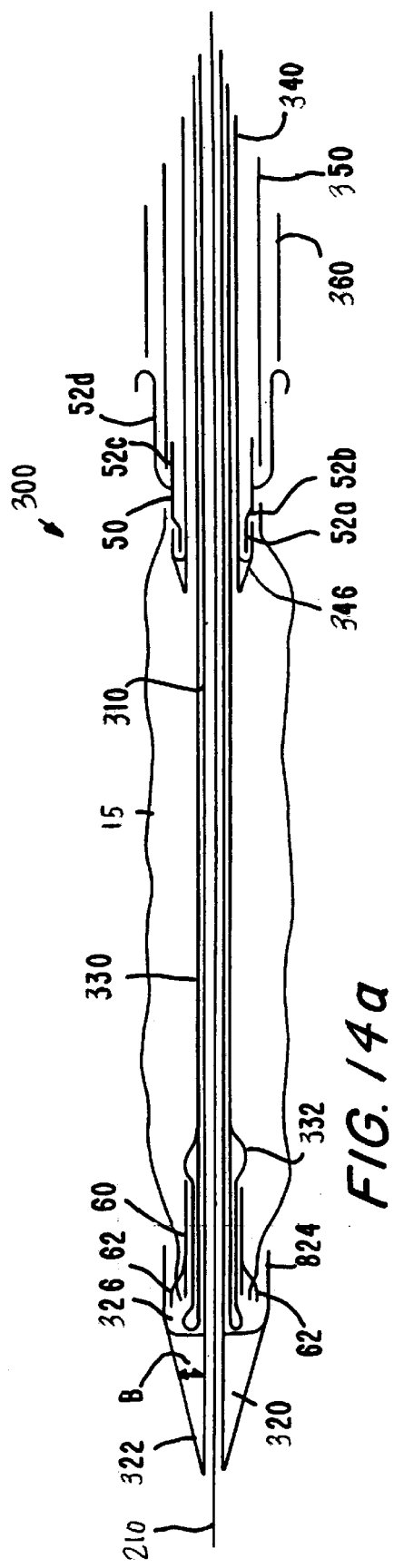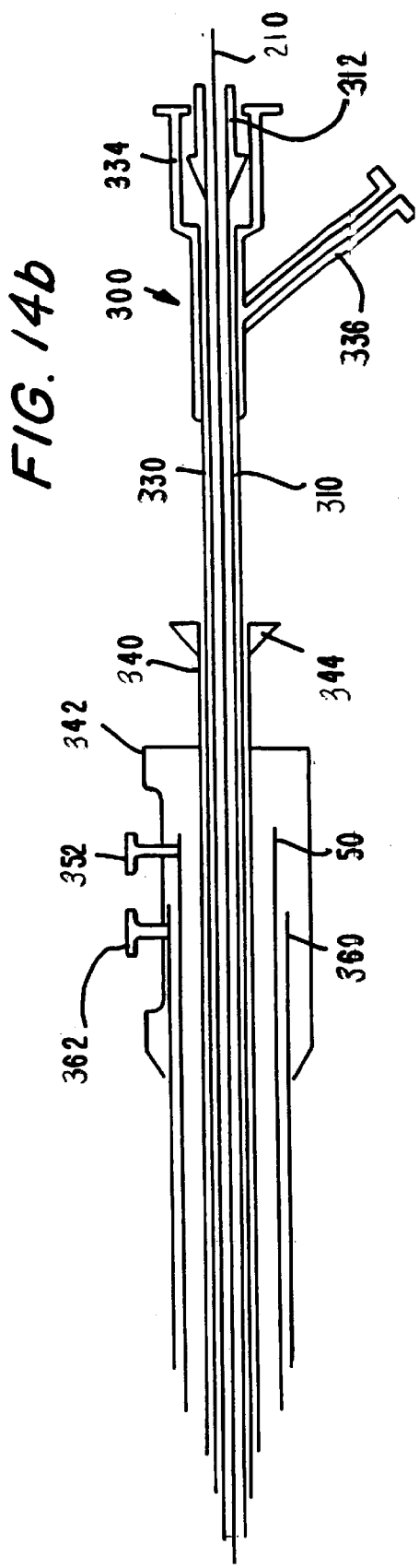

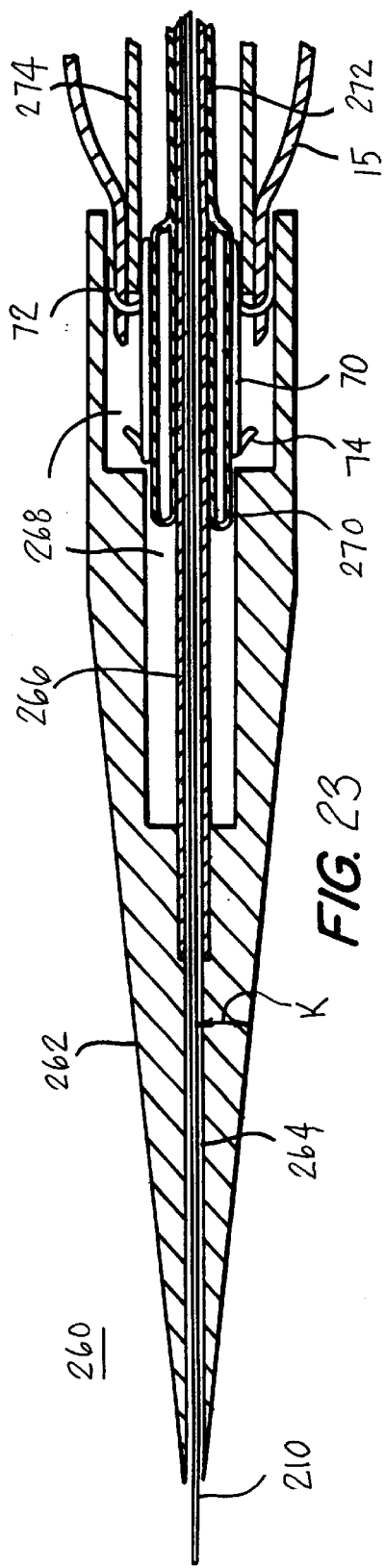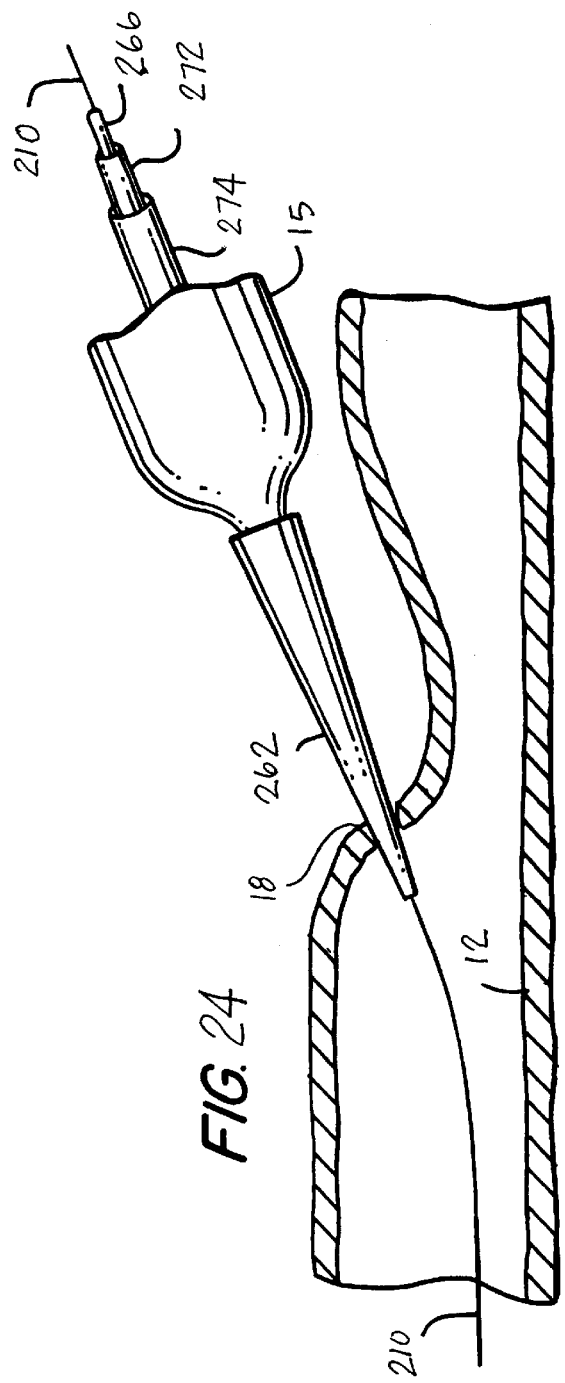

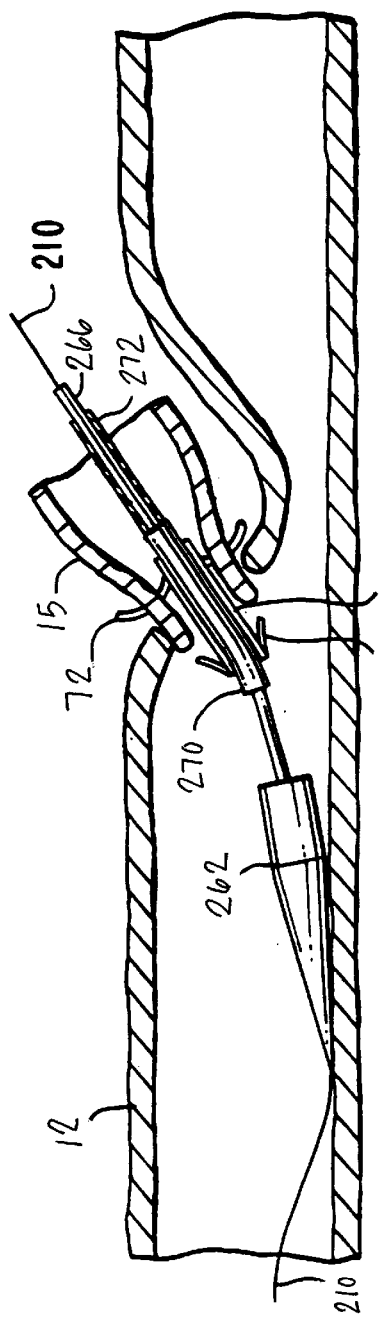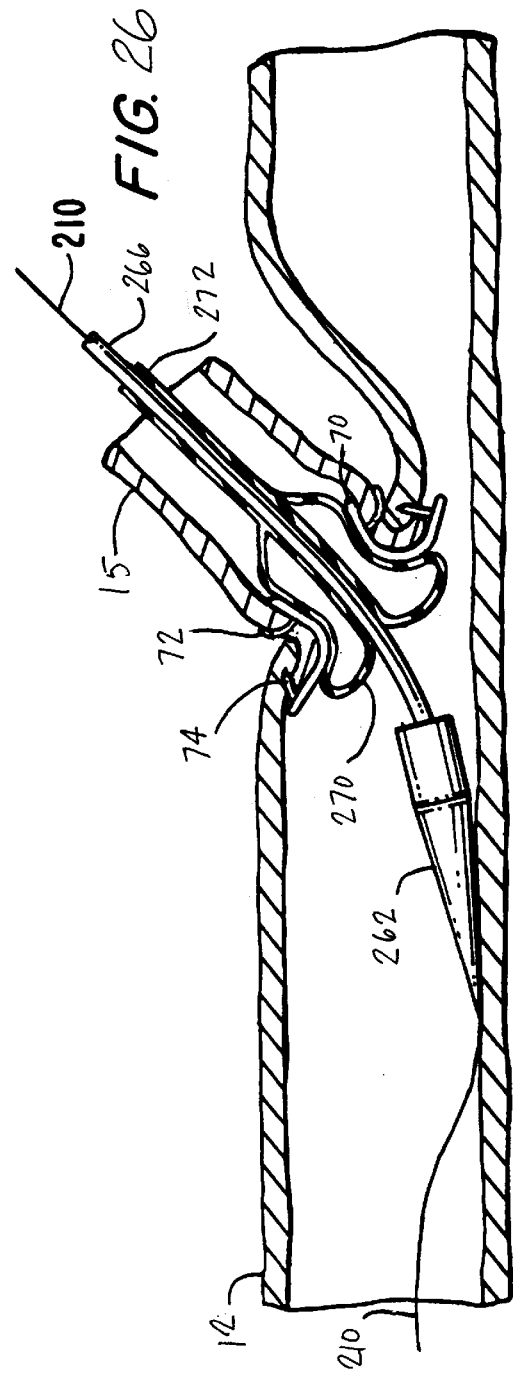

MEDICAL GRAFTING METHODS AND APPARATUS

This application claims the benefit of U.S. Provisional application No. 60/107,294, filed Nov. 6, 1998.

BACKGROUND OF THE INVENTION

This invention relates to medical grafting methods and apparatus, and more particularly to methods and apparatus for installing tubular bypass grafts primarily with intraluminal methods with the assistance of surgical and minimally invasive methods and apparatus.

A conventional bypass grafting technique is illustrated at FIG. 1, which shows a patient's aorta 10 with a coronary artery 12 branching off the aorta. A narrowing 14 in coronary artery 12 is restricting blood flow from aorta 10 to downstream portions of the coronary artery, thereby preventing the patient's heart from receiving all the blood it needs for normal operation. In more serious conditions, the coronary artery may be entirely occluded. To remedy this condition, a bypass graft around narrowing 14 is needed, and one way to provide such a bypass is to add a graft conduit 15 from aorta 10 (e.g., at location 16) to a downstream portion of coronary artery 12 (e.g., at location 18). Sutures 20 are typically applied to "proximal" anastomosis location 16, i.e., at the joining of a graft conduit 15 with the side wall of the aorta 10 and "distal" anastomosis site 18, i.e., at the joining of the graft conduit 15 with the side wall of the coronary artery 12. Failure of the bypass circuit often occurs at the anastomosis sites due to injury or to poor fluid dynamics. Such tissue stress may trigger a healing response that ultimately reduces the patency of the graft.

Conventional suturing techniques may contribute to the failure of the distal anastomosis. The sutures 20 themselves may initiate injury to the graft vessel at coronary anastomosis site, which is already in high stress. When veins, such as the saphenous vein, are used for graft material, the high arterial pressure may dilate the vein to a larger diameter than it would experience under typical venous pressure. At the anastomosis site, the combination of the sutures and the arterial pressure amplifies the stress on the tissue, resulting in tissue injury and reduced patency.

Typical conventional techniques nevertheless require that the patient's heart be stopped and the patient be placed on cardiopulmonary bypass (CPB) to oxygenate and circulate the blood during the procedure. Stopping of the heart and CPB is typically required to allow effective suturing of the anastomosis. Suturing also requires blood flow to be stopped for optimal anastomosis. As a result, the patient is placed on CPB to provide a bloodless field and a still heart for the surgeon to attach the graft vessels. However, it is known that CPB can be very time consuming, costly and dangerous to the patient. Complications may include emboli, blood degradation, and damage to tissue from the use of cannulas. Alternatives to CPB may include the cross-clamping of arteries, which may damage the vessels or dislodge deposits such as atherosclerotic plaque from the lining of the vessel walls.

Goldsteen et al. U.S. patent application Ser. No. 08/745, 618, filed Nov. 7, 1996, shows, among other things, methods and apparatus for installing tubular bypass grafts intraluminally. (The Goldsteen et al. reference is hereby incorporated by reference herein in its entirety.) The Goldsteen et al. reference shows methods and apparatus in which each end of the graft site is approached separately and intraluminally, penetrated, and then a longitudinal structure (e.g., element 150 in the Goldsteen et al. reference) is established between the ends of the graft site. This longitudinal structure may extend intraluminally all the way out of the patient's body from both ends of the graft site. The graft is fed into the patient's body intraluminally along the longitudinal structure until it is in the desired position extending from one end of the graft site to the other. Each end of the graft is then secured by anastomosis at the respective end of the graft site and the longitudinal structure is withdrawn from the patient.

In some cases, it may not be necessary or desirable to separately approach both ends of the graft site. Sullivan et al. U.S. patent application Ser. No. 08/844,992, filed Apr. 23, 1997, shows, among other things, methods and apparatus for allowing a longitudinal structure to be extended intraluminally to one end of a graft site. (The Sullivan et al. reference is hereby incorporated by reference herein in its entirety.) At that end of the graft site the longitudinal structure passes out of the body structure lumen and extends extraluminally to the other end of the graft site. At the other end of the graft site, the longitudinal structure re-enters the body structure lumen. The graft is introduced intraluminally along the longitudinal structure until it passes out of the body structure lumen at the first end of the graft site and extends to the second end of the graft site. Both ends of the graft are then secured by anastomosis at the respective opposite ends of the graft site, and the longitudinal structure is axially withdrawn from the patient.

Under some circumstances, it is preferable to dissect and relocate a vessel, such as an arterial blood source, in order to shift the vessel to the graft site. Sullivan et al. U.S. patent application Ser. No. 08/869,808, filed Jun. 5, 1997 shows methods and apparatus for shifting a vessel and performing an anastomosis intraluminally.

What is need are methods and apparatus that provide the limited trauma of intraluminal methods but which also provide greater access or visibility during certain steps in the bypass procedure.

It is therefore an object of this invention to provide improved methods and apparatus for intraluminal installation of alternative tubular connections, such as bypass grafts and connections.

It is a more particular object of this invention to provide methods and apparatus for intraluminally installing bypass grafts which use simplified intraluminal apparatus to make the graft connection with surgical assistance or surgical access.

It is another object of the invention to reduce the patient trauma and risk of emboli, cannulation, and cross-clamping.

It is another object of the invention to reduce the procedural time and cost for current procedures.

SUMMARY OF THE INVENTION

These and other objects of the invention are accomplished in accordance with the principles of the invention by providing methods and apparatus for installing a graft between first and second spaced locations on a tubular structure of a patient. Many steps in the procedure are performed intraluminally, that is, inserted into the patient's tubular body structure and advanced along the interior of the tubular body structure to the operative site. In addition, a surgical access opening may be provided to allow surgical assistance in completing one or more steps in the procedure.

An elongated structure may be passed into and along a lumen of the tubular body structure so that a distal portion of the elongated structure extends to the first location. A distal portion of the elongated structure is used to make a first aperture through the tubular body structure at the first location.

The surgical access opening may be provided in the patient adjacent the first and second locations. In a preferred embodiment of the subject invention, surgical instrumentation is inserted in the surgical access opening to provide assistance. For example, the surgical instrumentation may be used to move an elongated member from the first location to the second location.

In another preferred embodiment, surgical instrumentation inserted through the surgical access opening is used to complete a connection between the graft and the tubular body conduit. If the graft is passed intraluminally, e.g., through the elongated structure, the surgical instrumentation may be used to move an end portion of the graft from one location to the other location. Alternatively, the graft may be inserted to the operative site through the surgical access opening and its end portions moved to the first and second locations.

In yet another preferred embodiment, connectors are advantageously used to make the connection between the graft and the tubular body structure. A connector attached to an end portion of the graft and inserted intraluminally through the elongated structure may be inserted into the tubular body structure by the surgical instrumentation. Alternatively, a connector may be inserted into the surgical access opening and subsequently connected to the graft and the tubular body structure.

Further features of the invention, its nature and various advantages will be more apparent from the accompanying drawings and the following detailed description of the preferred embodiments.

BRIEF DESCRIPTION OF THE DRAWINGS

FIG. 2 is a simplified view of the patient, illustrating the operative region, in accordance with the invention.

FIG. 2a is a sectional view taken along line 2a—2a, illustrating the operative region, in accordance with the invention.

FIGS. 14a and 14b collectively comprise a simplified sectional view of an illustrative embodiment of further apparatus in accordance with the invention. FIGS. 14a and 14b are sometimes referred to collectively as FIG. 14.

FIG. 23 is a simplified sectional view of an alternative embodiment of apparatus shown in FIG. 14, in accordance with the invention.

FIG. 24 is a simplified elevational view, partly in section, showing an early stage in use of the FIG. 23 apparatus in accordance with the invention.

FIG. 25 is a view similar to FIG. 24, but with more elements shown in section, and showing a later stage in use of the FIG. 23 apparatus in accordance with the invention.

FIG. 26 is a view similar to FIG. 25 showing a still later stage in use of the FIG. 23 apparatus in accordance with the invention.

DETAILED DESCRIPTION OF THE PREFERRED EMBODIMENTS

Figure 1:
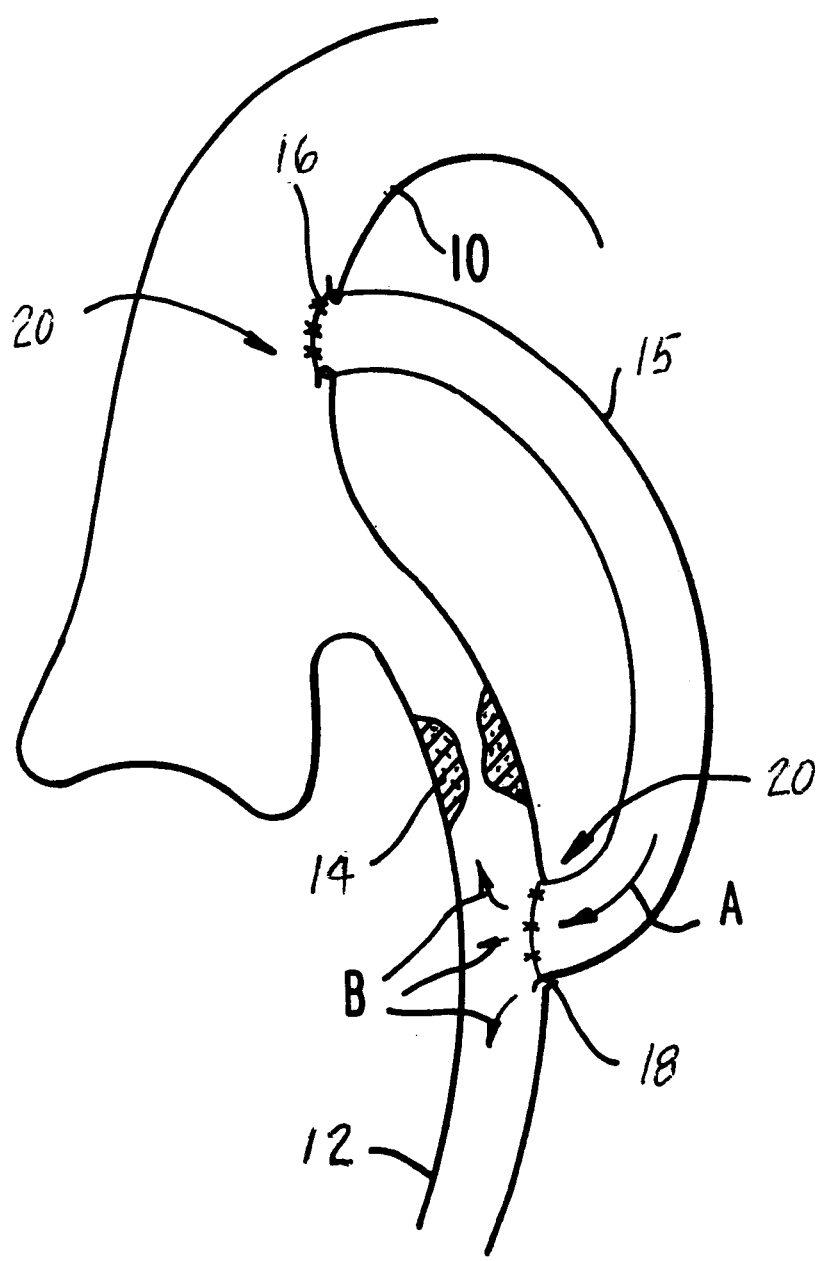
FIG. 1 is a simplified schematic view of the prior art anastomosis technique, in accordance with the invention.

Although the invention has other possible uses, the invention will be fully understood from the following explanation of its use in providing a bypass around a narrowing in a patient's vascular system.

The procedure and apparatus to perform the bypass graft contemplate intraluminal delivery and manipulation of instrumentation, supplemented by surgical assistance introduced through surgical openings in the patient's body, such as conventional medial sternotomy, or preferably through minimally invasive procedures involving small incisions or cannulas or trocars placed on the chest.

Surgical access provides improved visibility to the physician during the procedure. It may also allow management of bleeding by the introduction of equipment to remove blood from the operative cavity as well the introduction of equipment to irrigate the region. This approach also allows for the removal of inconsequential tissue such as fascia and fat from the anastomosis sites. Providing a surgical opening creates greater access to the physician under certain circumstances. For example, where suturing is the preferred method of making the anastomosis, surgical access provides the physician with room to introduce suturing equipment, and with room to manipulate the suturing equipment and apply the sutures. Where bypass procedure involves the redirecting of a vessel, such as the IMA, surgical access simplifies the "take down" process, or dissection of the vessel from surrounding tissue.

Accordingly, the region above the operative site on the skin surface of the patient is located. As illustrated in FIG. 2, the location of heart 100 in the chest of the patient 102 is found, as is the location of individual ribs 104. An incision is made in the chest, in the intercostal space between the ribs 104 of the patient 102. Although reference is made to a single incision, it is contemplated that several incisions and access points may be made. A trocar tube or cannula 106 is placed in the incision to facilitate the introduction and removal of surgical instrumentation (FIG. 2a).

If further accessibility is required, a portion of the connective tissue and cartilage between the ribs may be removed to view the operative region and allow access for surgical instrumentation. In another embodiment, a retractor clamp (not shown) may be applied to the incision to hold it in an open position. In a further alternative embodiment, the retractor clamp may be configured to partially deflect the ribs apart. In yet another alternative where more accessibility is required, one or more of the ribs may be cut adjacent the sternum and deflected. All of these methods of surgically accessing the region adjacent the heart. may be less traumatic on the patient than the conventional medial sternotomy. The terms "access trocar" or "surgical access openings" will be used throughout the following description and will refer to any of the preceding minimally invasive access means deemed appropriate by the physician for the particular procedure and patient history. In a preferred embodiment of the invention, a viewing scope, such as a thoracoscope, is inserted through incision to assist in observing the procedure as it is carried out as described below. In addition, apparatus for sucking fluid, such as blood, from the operative site, may be inserted in the surgical access opening, e.g., to control bleeding.

Figure 3:
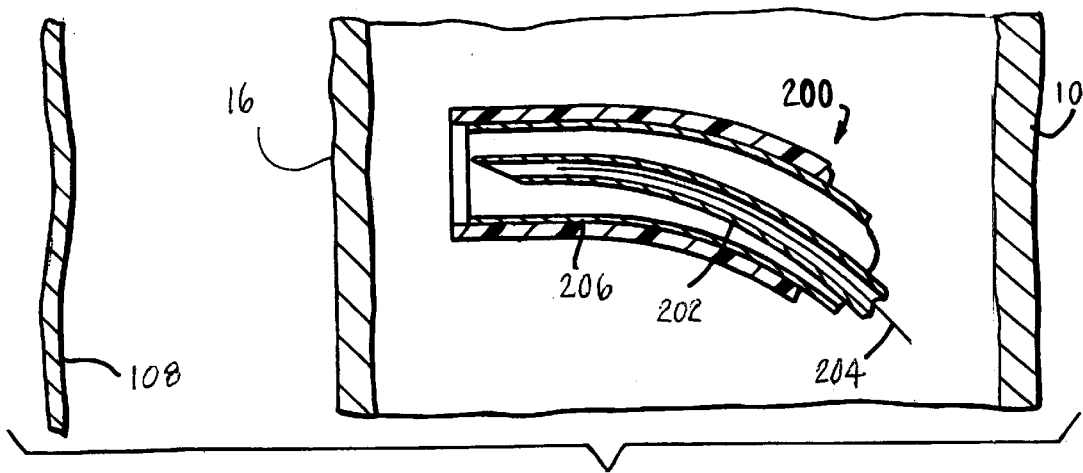
FIG. 3 is a sectional view showing an early stage in the use of illustrative apparatus and methods in accordance with the invention.

An early stage in an illustrative graft installation procedure, such as a coronary artery bypass procedure, in accordance with the invention includes accessing a first location 16 on the patient's tubular body structure, such as the aortic end of the desired bypass around narrowing 14. (See also Berg et al. U.S. patent application Ser. No. 09/014,759, filed Jan. 28, 1998 and Berg et al. U.S. patent application Ser. No. 09/187,364, filed Nov. 6, 1998, both hereby incorporated by reference herein in their entirety, for additional and/or alternative apparatus and/or methods usable in the aortic access that will now be described.) Catheter or catheter-like structure 200 is introduced intraluminally into the patient's circulatory system and advanced to the aorta 10 as shown in FIG. 3. Catheter 200 is preferably introduced into the patient at a location remote from the coronary area. For example, catheter 200 may be introduced into the patient via a femoral artery. The distal portions of catheter 200 are preferably remotely controlled from proximal portions of the apparatus which remain outside the patient at all times.

Figure 4:
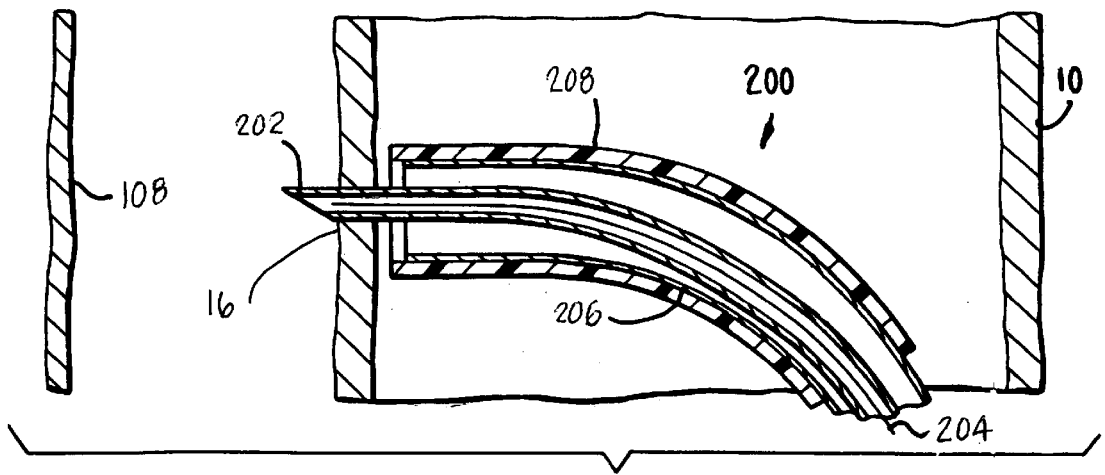
FIG. 4 is another sectional view similar to FIG. 3 showing a later stage in use of illustrative apparatus and methods in accordance with the invention.
Figure 5:
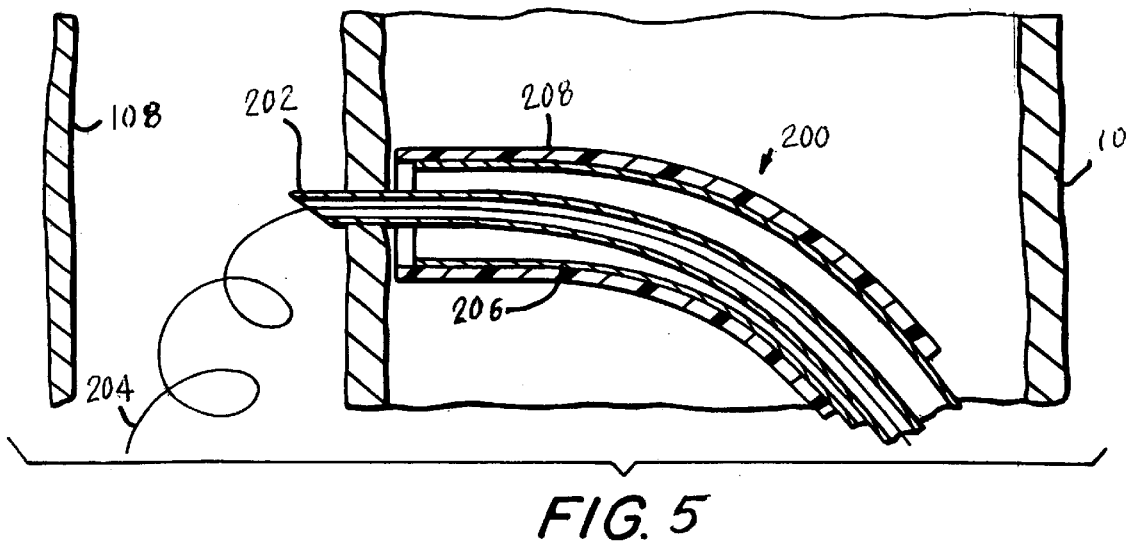
FIG. 5 is another sectional view similar to FIG. 3 showing a still later stage in use of illustrative apparatus and methods in accordance with the invention.

A preferred construction of catheter 200 is shown in FIGS. 3–8. (See also U.S. patent application Ser. No. 09/187,364 incorporated by reference above, and Berg et al. U.S. patent application Ser. No. 09/010,367, filed Jan. 21, 1998 and hereby incorporated by reference herein in its entirety, for possible additional and/or alternative features for catheter 200.) Catheter 200 is pushed into the patient until its distal portion is adjacent the inside surface of the wall of the aorta 10 near location 16 where it is desired to connect the aortic end of the bypass graft around narrowing 14 (see FIG. 3). Needle catheter 202 is then pushed distally so that its sharpened distal end portion passes through the wall of aorta 10 at location 16 as shown in FIG. 4. Needle catheter 202 may be provided with barbs (not shown in the FIGS.) at a distal portion thereof which secure the adjacent aortic tissue, as will be described below. The next step is to push the distal portion of pilot wire 204 out of the distal end of needle catheter 202 and into the space between aorta 10 and pericardial membrane 108 as shown in FIG. 5.

Figure 6:
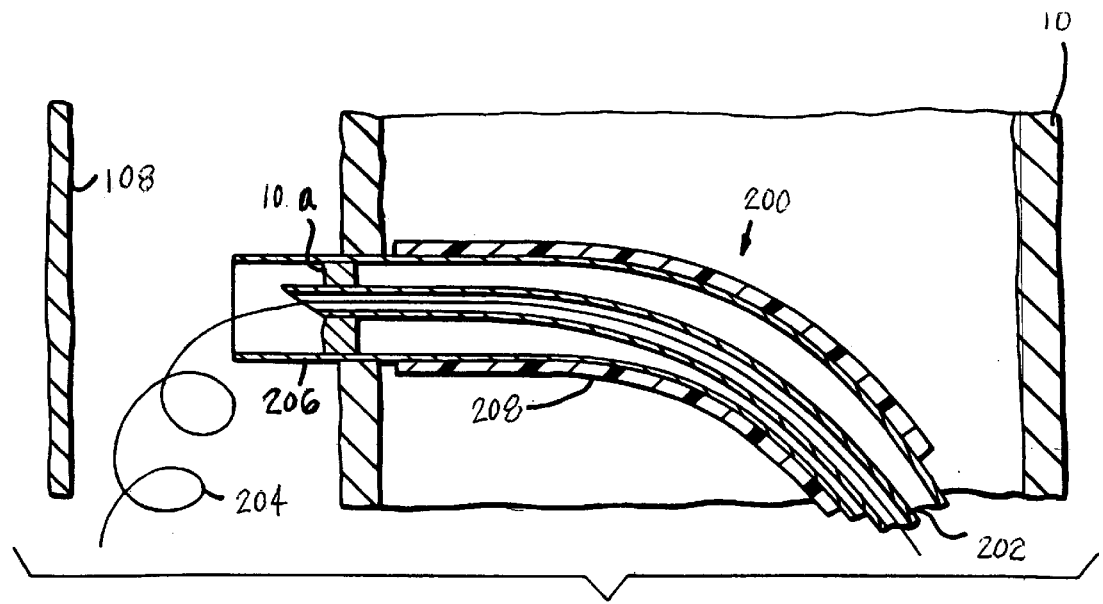
FIG. 6 is another sectional view similar to FIG. 3 showing an even later stage in use of illustrative apparatus and methods in accordance with the invention.

Subsequently, cutter catheter 206 is pushed in the distal direction so that a sharpened distal end of catheter 206 makes an annular cut through the wall of aorta 10 as shown in FIG. 6, thus forming a portion 10a of aortic tissue 10. (If barbs have been provided on the distal portion of needle catheter 202, such barbs may prevent the portion 10a of aortic tissue from being released into the patient's bloodstream.) The distal portion of cutter catheter 206 tends to follow pilot wire 204 in the space between aorta 10 and pericardial membrane 108 to prevent cutter catheter 206 from inadvertently cutting through membrane 108. The cutter catheter shaft functions as a plug through the aperture in the aorta wall that the cutter catheter has formed. This prevents blood flow-from the aorta into the pericardial space.

Figure 7:
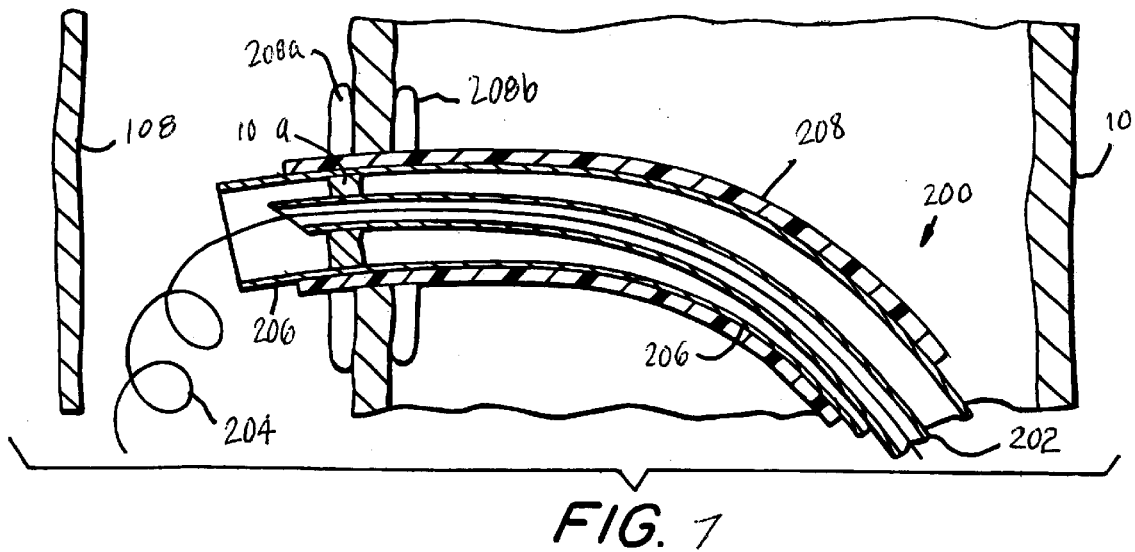
FIG. 7 is another sectional view similar to FIG. 3 showing a still later stage in use of illustrative apparatus and methods in accordance with the invention.
Figure 8:
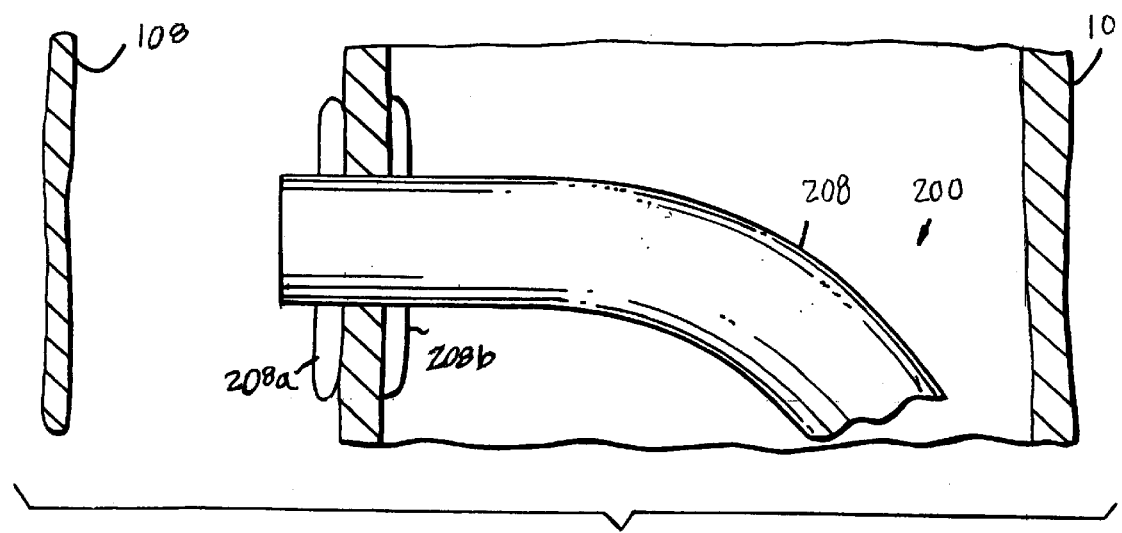
FIG. 8 is another sectional view similar to FIG. 3 showing an even later stage in use of illustrative apparatus and methods, with certain apparatus removed, in accordance with the invention.

The next step is to push the distal portion of aortic access catheter 208 through the aperture in the aorta wall that the cutter catheter has formed as shown in FIG. 7. The aortic access catheter 208 is sized slightly larger in diameter than the cutter catheter 206 to make use of the elastic recoil of the aorta, which helps seal the aortic opening around catheter 208, thereby ensuring no blood leakage into the pericardial space while catheter 208 is positioned through the aorta wall. If the aorta wall does not provide sufficient elastic recoil, selectively inflatable annular sealing balloons 208a and/or 208b can be added to catheter 208 to provide sealing or to help anchor the distal end of catheter 208 through the aperture in the aorta wall. When catheter 208 is satisfactorily placed in aorta 10, the physician may withdraw catheter 206, cannula 202, and wire 204, as illustrated in FIG. 8 (see, for example, Berg et al. U.S. patent application Ser. No. 09/010,367, filed Jan. 21, 1998, which is hereby incorporated by reference herein in its entirety).

Figure 9:
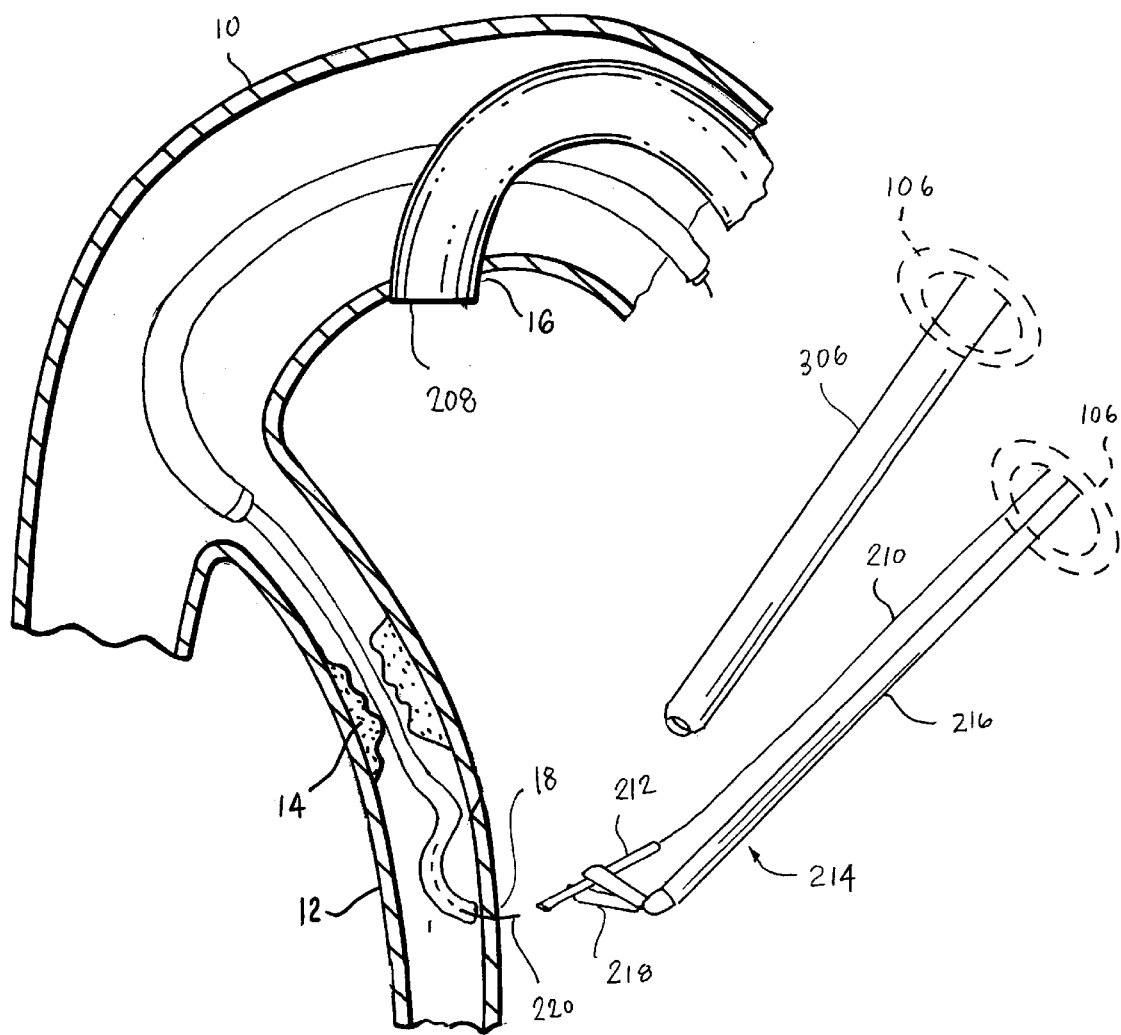
FIG. 9 is a simplified longitudinal view showing a portion of an illustrative procedure and related apparatus, in accordance with the invention.

A further step in accordance with the invention relates to introducing an elongated guide member 210 into the patient. Elongated guide member is primarily a metal wire or wire-like structure. As illustrated in FIG. 9, as described above, the surgical access opening 106 has been provided. The guide member 210 is introduced into the surgical access opening 106 and advanced to the operative site adjacent the two desired anastomosis locations, i.e., the aortic access location (i.e., the proximal anastomosis site) 16 and the coronary artery access location (i.e., the distal anastomosis site) 18.

According to a preferred embodiment, the guide member 210 is introduced through the surgical access opening 106 with a cannula needle 212 positioned adjacent the distal end. In one embodiment, the cannula needle 212 may be held by a surgical instrument, such as grasper 214, which may be configured to hold and to guide the cannula needle 212 and the guide member 210 to the distal anastomosis site 18. Where surgical access is limited, such as by a trocar or small incision, grasper 214 is preferably sized for entry into the incision and configured with an elongated body portion 216 and a handle portion (not shown) adjacent the proximal end for remotely actuating the distal grasping portion 218. A remote viewing apparatus, such as endoscope 306 may be provided through surgical access opening 106 to view the procedure.

According to one embodiment of the invention, A marker wire 220, may be intraluminally introduced to the operative site. In a preferred embodiment, a marker wire 220 is coaxially advanced along the patient's circulatory system through and past the narrowing 14 to the proposed distal anastomosis site 18. Marker wire 220 may be a catheter, such as the catheter described in U.S. patent application Ser. No. 09/187,364 (293/036), filed Nov. 6, 1998, which is incorporated by reference in its entirety herein. The marker wire 220 is preferably loaded with conventional radiopaque filler to help the physician locate and properly orient the wire in the patient's artery.

With continued reference to FIG. 9, marker wire 220 is used to pierce wall of the coronary artery 12 at the desired location from inside the vessel to the outside to mark the location for the anastomosis. The surgical instrumentation 214 may be used to move the cannula needle 212 and the elongated guide member 210 to the anastomosis location as clearly indicated to the physician by the location of marker wire 220.

Figure 11:
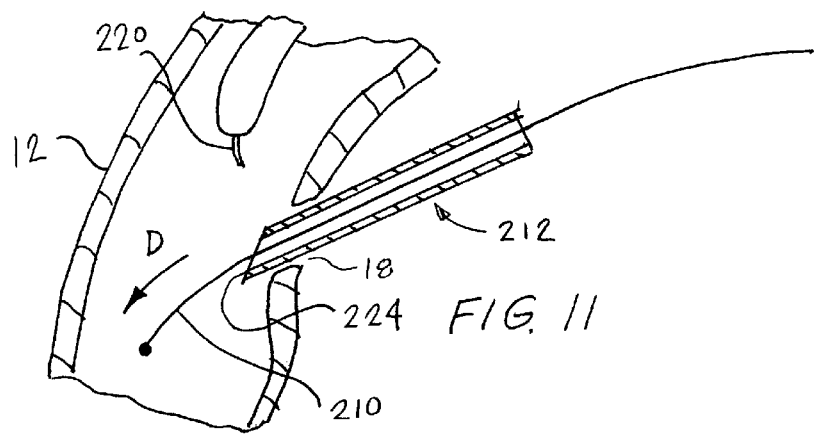
FIG. 11 is another enlarged sectional view similar to FIG. 10 showing a later stage in use of illustrative apparatus and methods in accordance with the invention.
Figure 12:
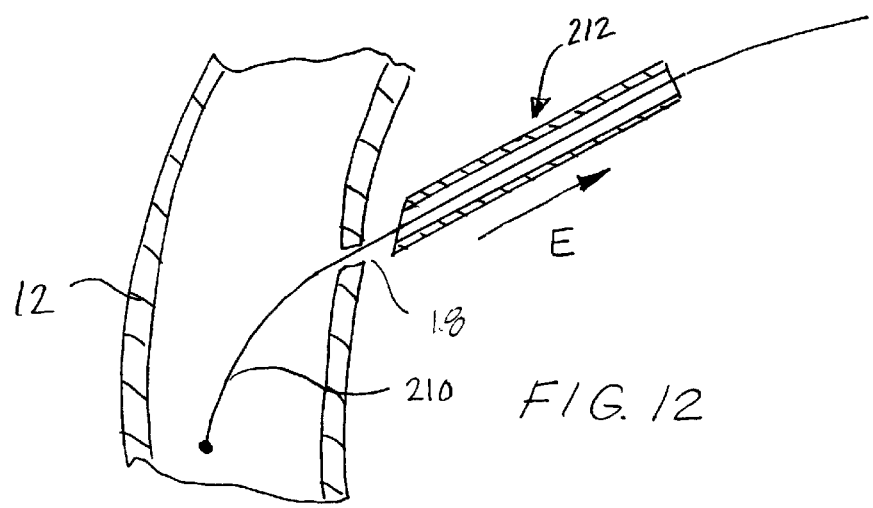
FIG. 12 is another enlarged sectional view similar to FIG. 10 showing a still later stage in use of illustrative apparatus and methods in accordance with the invention.

As a later step illustrated in FIG. 10, marker wire 220 may be withdrawn into the vessel, as indicated by arrow C. Cannula needle 212 may have a hollow configuration including a narrow body portion 222 and a sharpened tip 224, which passes through the wall of the coronary artery 12 at the location 18 pierced by the marker wire 220 and extends partially into the coronary artery 12. Subsequently, as FIG. 11 illustrates, the distal end of the guide member 210 is extended from the tip 224 of the cannula needle 212 into the lumen of the coronary artery 12, as indicated by arrow D. Cannula needle 212 may be withdrawn from coronary artery 12, as indicated by arrow E, leaving the elongated guide member 210 in position within the coronary artery 12 (FIG. 12).

In an alternative embodiment, the marker wire may remain within the coronary artery adjacent the desired anastomosis location, without piercing through the wall. Under such circumstances, the cannula needle, which has a sharpened coring configuration, could be used to pierce the coronary artery wall, and the end of the guide wire subsequently deployed into the coronary artery. The guide wire may be advanced further downstream into the coronary artery until it is secured in place. As an alternative or supplement to the radiopaque marker described above, a standard thoracoscope may be introduced to locate the anastomotic site and/or to view the procedure. Alternatively, the physician may locate the desired anastomosis location by direct visualization or other means known in the art.

Figure 13:
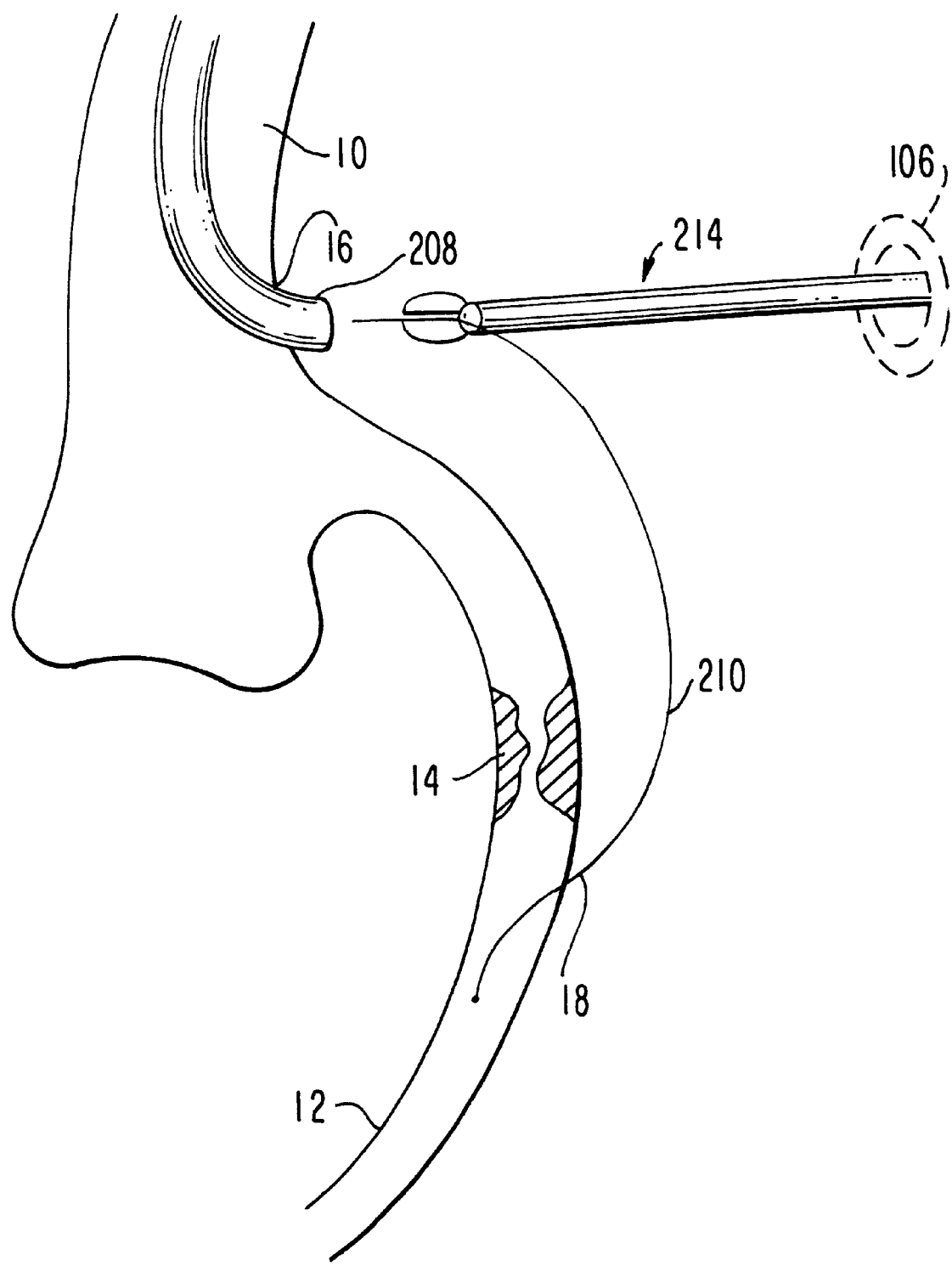
FIG. 13 is a simplified longitudinal view, similar to FIG. 9, illustrating a later stage in the use of illustrative apparatus and methods in accordance with the invention.

As illustrated in FIG. 13, a further step in the installation of the elongated guide member 210 is the positioning of the proximal end portion 211 thereof. The proximal end portion 211 of the guide wire may be held by surgical apparatus such as grasper 214. If there is sufficient access, the physician may alternatively grasp the proximal end of the guide wire by hand. The guide member 210 is inserted into the open end of the aortic access catheter 208, and advanced along the interior the catheter 208. The guide member 210 may subsequently exit the patient at the entry location of the catheter 208 as described above.

The process of installing the elongated guide member 210 as described above is exemplary. It is understood that the proximal end of the guide wire may be first installed within the aortic access catheter 208 prior to insertion of the distal end portion at the coronary artery. It is also contemplated that both ends of the guide wire may be installed simultaneously, for example, using two or more surgical instruments.

After the guide member has been positioned between the two anastomotic sites, the graft 15 may be delivered over the guide wire 210 to the desired location. An illustrative embodiment of a tubular graft 15 and structure 300 for delivering and installing the graft along guide member 210 is shown in FIG. 14 (which comprises FIGS. 14a and 14b connected between the right in FIG. 14a and the left in FIG. 14b) and described in U.S. patent application Ser. No. 09/187,364 (293/036), incorporated by reference above. Graft 15 is shown in FIG. 14 with a connector 50 at its proximal end for use in connecting the graft to the side wall of the patient's aorta 10. Connector 50 may be of a type shown in commonly assigned, concurrently filed U.S. patent application Ser. No. 09/187,335, filed Nov. 6, 1998 (293/ 037), which is hereby incorporated by reference herein in its entirety. Graft 15 is also shown in FIG. 14 with a connector 60 at its distal end for use in connecting the graft to the patient's coronary artery 12. Connector 60 may be of a type shown in commonly assigned, concurrently filed U.S. patent application Ser. No. 09/187,361, filed Nov. 6, 1998 (293/ 038), which is hereby incorporated by reference herein in its entirety.

Graft 15 is assumed to be a length of the patient's saphenous vein which has been harvested for use in the coronary artery bypass procedure being described. It will be understood however, that other natural body conduit can be used for graft 15, or that graft 15 can be a synthetic graft or a combination of natural and synthetic materials. It will also be understood that the particular connectors 50 and 60 shown in FIG. 14 are only illustrative and that other connectors can be used instead if desired. For example, connectors of the type shown in commonly assigned, William J. Swanson et al. U.S. patent application Ser. No. 09/186,774 (293/039), filed Nov. 6, 1998, which is hereby incorporated by reference herein in its entirety, can be used for distal (coronary artery) connector 60. Connectors of the type shown in above-mentioned application Ser. No. 09/187,335 (293/037) can also be used for distal connector 60.

Tube 310 is configured for disposition substantially concentrically around elongated guide member and for sliding axially along that structure. Proximal actuator structure 312 and distal tip structure 320 are secured to tube 310 at respective opposite ends thereof. Distal tip structure 320 has a substantially conical distal-most outer surface portion 322 to gradually enlarge the aperture through the epicardial membrane and the side wall of coronary artery 12 and thereby enter the artery without the artery collapsing as a result of too much force being applied to the exterior. Tip structure 320 includes an annular recess 326 in its proximal portion for receiving the distal-most portions of structure 330/332 (described below), connector 60, and graft conduit 15.

Tube 330 is disposed substantially concentrically around tube 310 and is slidable axially relative to tube 310. Annular balloon 332 is secured to a distal portion of tube 330. Actuator structure 334 and luer connector 336 are secured to a proximal portion of tube 330. The side wall of tube 330 preferably includes a lumen (not shown) which extends from connection 336 to the interior of balloon 332 so that the balloon can be inflated or deflated by appropriately directed fluid flow through that lumen. Balloon 332 is shown deflated in FIG. 14. Tube 330 is again sufficiently laterally flexible to allow structure 300 to follow whatever path guide member has in the patient.

Connector 60 is disposed annularly around balloon 332. In FIG. 14 connector 60 has its initial, relatively small, circumferential size. Fingers 62 extend radially out from the main portion of connector 60 in order to pass through the distal end portion of graft conduit 15 and thereby secure the graft to the connector. Other graft-to-connector securing means such as sutures may be used instead of or in addition to fingers 62. Connector 60 can be plastically circumferentially enlarged by inflation of balloon 332 as described below when tip structure 320 is shifted distally relative to balloon 332 to fully expose elements 332 and 60 and the distal end portion of graft conduit 15. In the condition shown in FIG. 14, however, tip structure 320 shields and protects elements 332, 60, and 15 and provides a smooth profile for facilitating entry of these elements into the patient's coronary artery through an aperture in the side wall of that artery (see the following discussion of use of apparatus 300). Additional details regarding suitable constructions of connector 60 will be found in above-mentioned application Ser. No. 09/187,361 (293/038).

The components of structure 300 that have thus far been described are particularly associated with positioning and control of distal connector 60. The further components of structure 300 that will now be described are particularly associated with positioning and control of proximal connector 50.

Tube 340 is disposed substantially concentrically around tube 330. Tube 340 is slidable axially along tube 330 by proximal actuator 342, but preferably includes a proximal structure 344 (e.g., a collet-type structure) for allowing tube 340 to be releasably locked to tube 330 at various axial locations along tube 330.

Annular connector 50 is shown in FIG. 14 in its initially relatively small circumferential size. Connector 50 is resiliently biased to circumferentially enlarge to a larger final circumferential size, but is prevented from doing so by the surrounding distal cone portion 346 of tube 340. Most of connector 50 is disposed annularly around tube 340, but distal portions 52a of the connector enter a proximal-facing annular recess in cone portion 346 which helps to maintain the initial small circumferential size of the connector.

Proximal of portions 52a connector 50 includes radially outwardly extending graft retention fingers 52b that pass through the proximal end portion of graft conduit 15 to secure the connector to the graft conduit. Other graft-to-connector securing means such as sutures can be used instead of or in addition to fingers 52b.

Still more proximal of fingers 52b connector 50 includes "inside" fingers 52c and "outside" fingers 52d. Inside fingers 52c are resiliently biased to spring radially out, but are initially held relatively parallel to the longitudinal axis of structure 300 by being confined inside a distal end portion of tube 350. Outside fingers 52d are also resiliently biased to spring radially out, but are initially held relatively parallel to the longitudinal axis of structure 300 by being confined inside catheter 200 (which is already in place in the patient as shown, for example, in FIG. 30). Tube 350 is disposed substantially concentrically around tube 340 and is axially slidable relative thereto by proximal actuator 352. Tube 360 is disposed substantially concentrically around tube 350 and is axially slidable relative thereto by proximal actuator 362. The distal end of tube 360 is axially aligned with proximal portions of fingers 52d. Each of tubes 340, 350 and 360 is sufficiently laterally flexible so as not to interfere with the ability of structure 300 to follow any path that structures 200 and 600 have in the patient. Each of tubes 340, 350, and 360 is also axially strong enough to transmit necessary forces axially along the tube between the associated proximal actuator 342, 352, or 362 and the operative distal end portion of the tube. As has been mentioned, additional details of suitable constructions for connector 50 can be found in above-mentioned application Ser. No. 09/187,335 (293/ 037).

Figure 15:
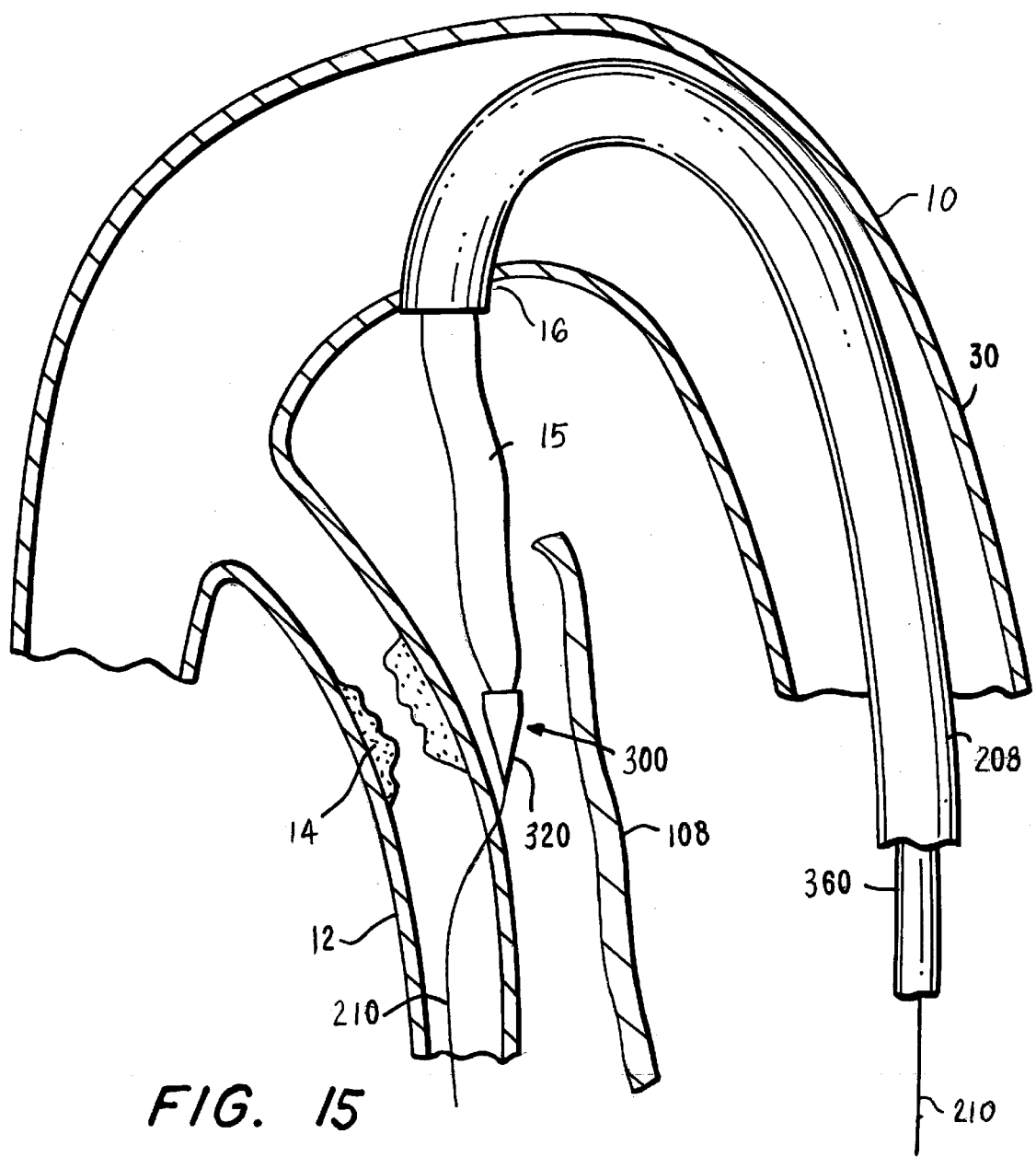
FIG. 15 is a view similar to FIG. 9, showing use of the apparatus of FIG. 14.

Structure 300, with a suitable length of graft 15 and associated connectors 50 and 60 mounted thereon as shown in FIG. 14, is inserted axially into the patient along guide member 210 and inside catheter 208 as shown in FIG. 15. At the distal end of catheter 208 at location 16, the distal portion of structure 300 emerges from the catheter and therefore from the patient's aorta 10 and continues to follow structure 210 toward the side wall of the patient's coronary artery 12.

Figure 16:
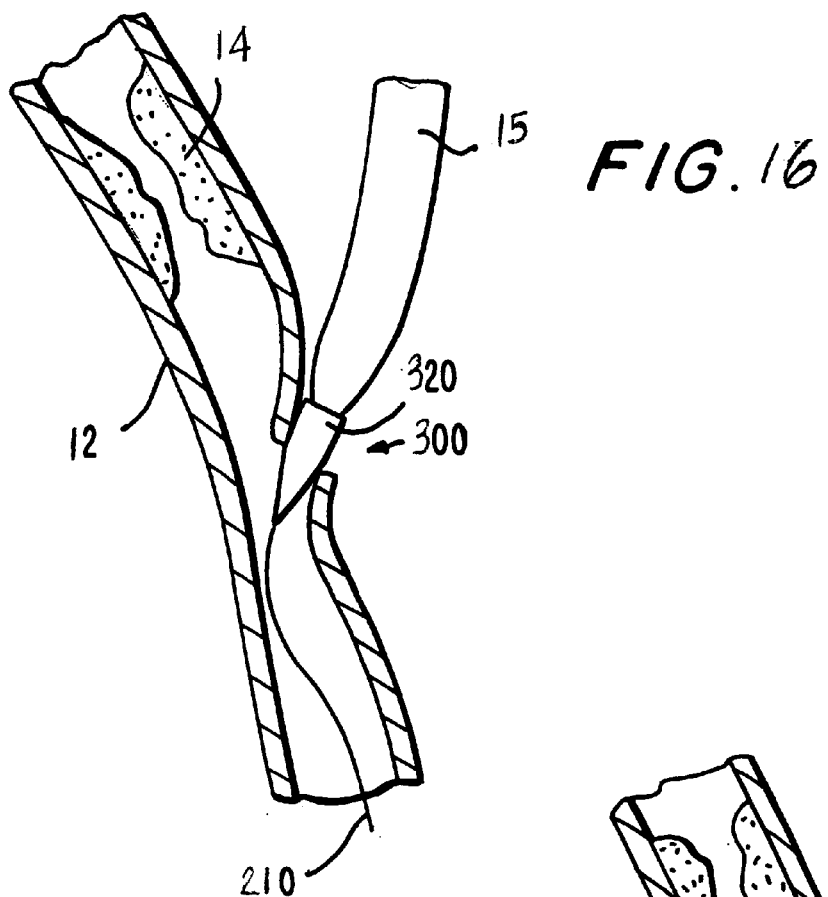
FIG. 16 is a view similar to a portion of FIG. 15 showing a later stage in use of the FIG. 14 apparatus.

Continued distal pushing of structure 300 axially along guide member 210 causes the conical distal tip 320 of structure 300 to begin to penetrate the side wall of the coronary artery 12 as shown in FIG. 16, thereby gradually enlarging the aperture in the coronary artery side wall previously occupied solely by guide member 210. Structure 300 continues to be pushed distally until distal tip structure 320 is entirely inside the coronary artery, as is connector 60 and the distal portion of graft 15. Then tube 330 is held stationary while tube 310 continues to be pushed distally. This causes distal tip structure 320 to separate from connector 60 and the associated distal portions of graft 15 and structure 330/332 (see FIG. 17).

Figure 17:
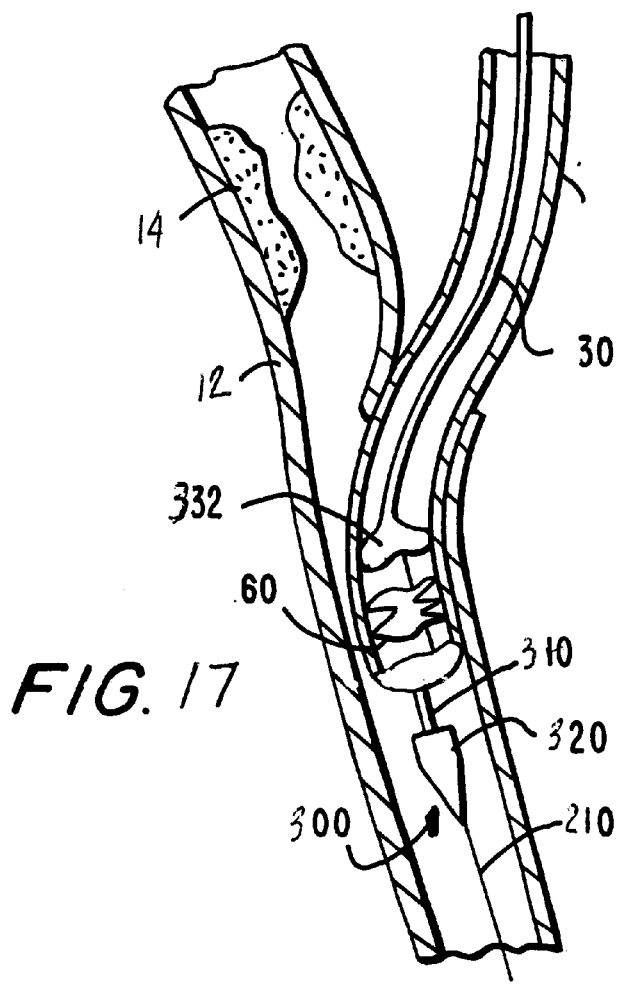
FIG. 17 is a view similar to FIG. 16 showing a still later stage in use of the FIG. 14 apparatus.

Balloon 332 is then inflated to circumferentially plastically enlarge connector 60 as shown in FIG. 17. Connector 60 thereby presses the surrounding distal portion of graft 15 radially out against the inner surface of the coronary artery wall, which both holds the distal end of the graft inside the coronary artery and provides a hemodynamic seal between the graft and the coronary artery. If desired, connector 60 can be long enough to extend upstream inside graft 15 and out the aperture in the coronary artery side wall to help hold open the graft where it passes through that aperture and to help the graft seal the aperture. After connector 60 has been thus radially enlarged, balloon 332 can be deflated again.

Alternatively, it is contemplated that graft 15 may be connected to vessel 12 with conventional sutures. If the surgical access opening is sufficiently large, the physician may apply the sutures manually in a conventional manner. Alternatively, the surgeon may rely on the assistance of laparoscopic instrumentation to apply the sutures to the material.

Figure 18:
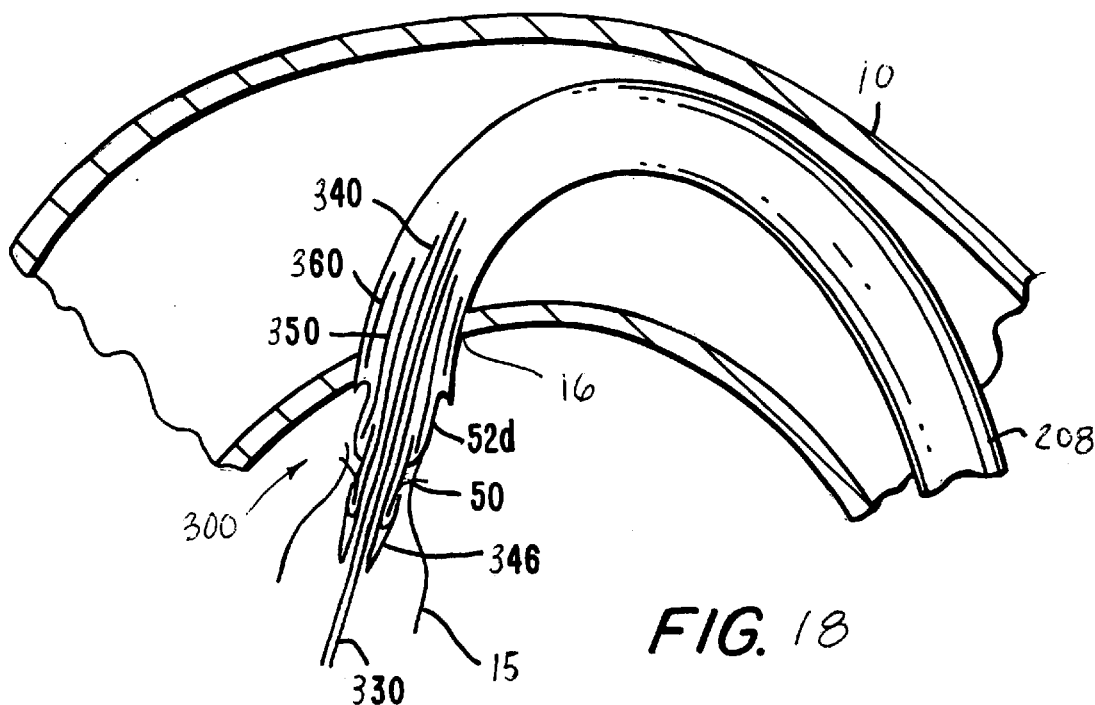
FIG. 18 is a view similar to another portion of FIG. 15 showing a stage in use of the FIG. 14.

FIG. 18 illustrates the condition of the portion of structure 300 in the vicinity of connector 50 when the distal portion of the apparatus is as shown in FIG. 17. In particular, outside fingers 52d of connector 50 are preferably just outside the side wall of aorta 10.

Figure 19:
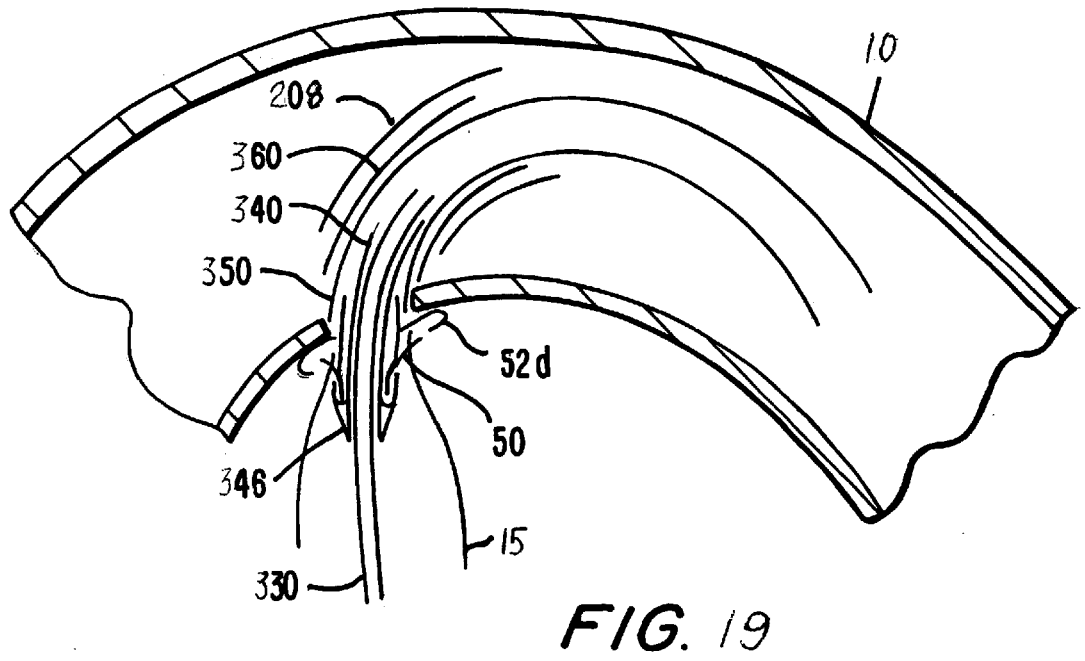
FIG. 19 is a view similar to FIG. 18 showing an even later stage in use of the FIG. 14 apparatus.

The next step is to proximally retract catheter 208 while holding tubes 340, 350, and 360 stationary. This releases outside fingers 52d to spring radially out as shown in FIG. 19. Tube 340 can then be pulled proximally back somewhat to snug fingers 52d up against the wall of aorta 10 as is also shown in FIG. 19.

Figure 20:
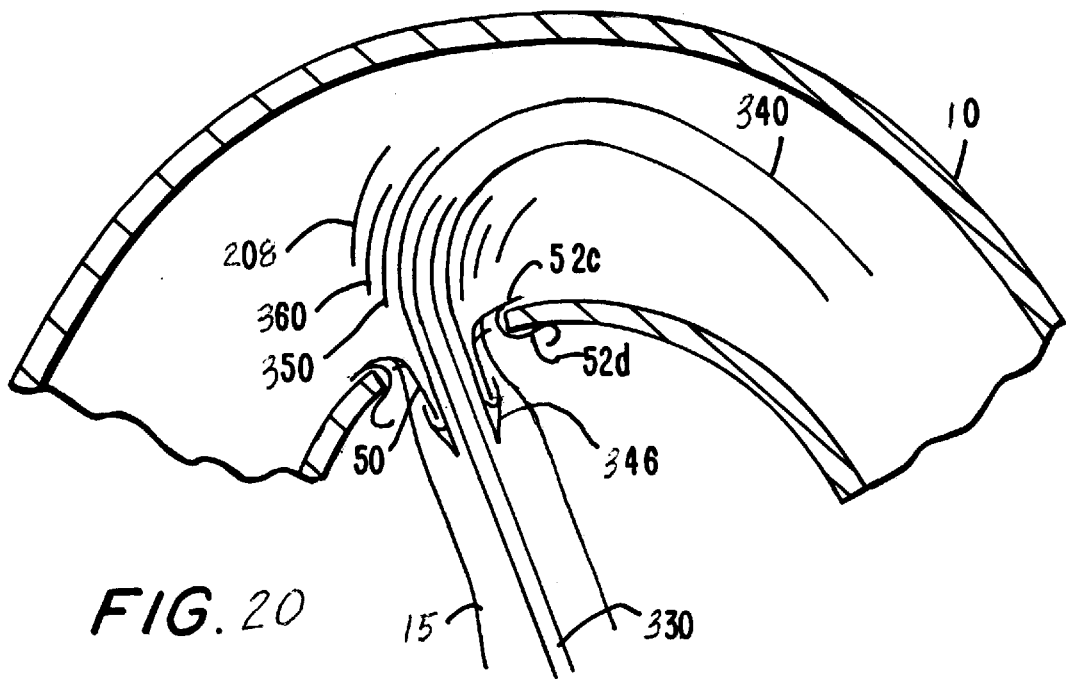
FIG. 20 is a view similar to FIG. 19 showing a still later stage in use of the FIG. 14 apparatus.
Figure 21:
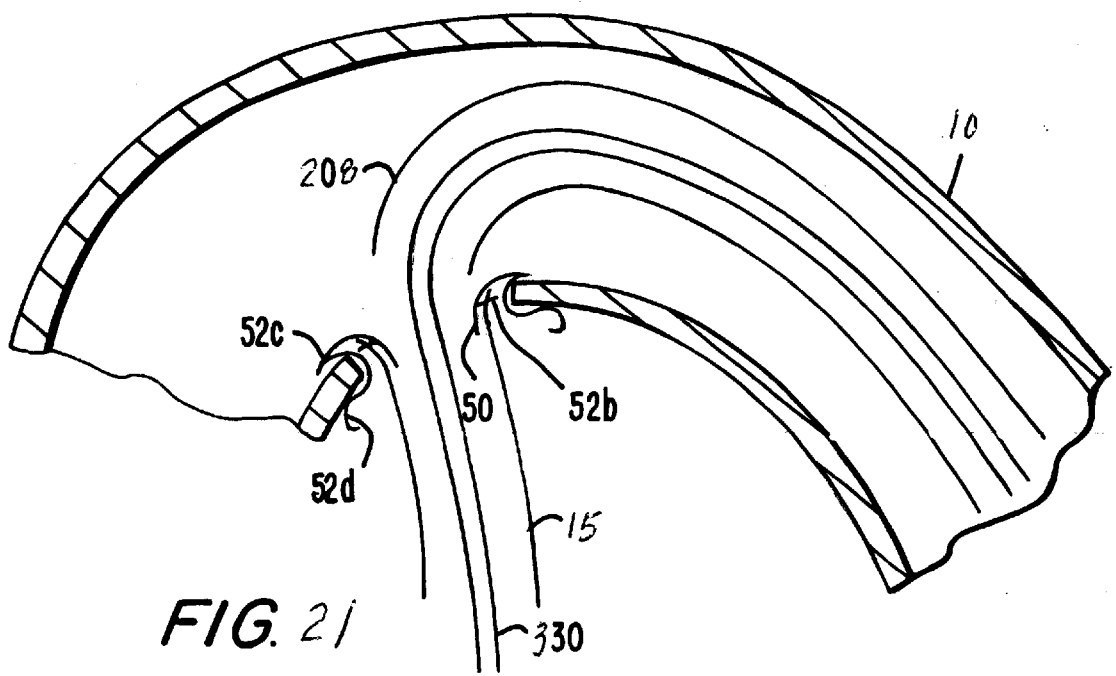
FIG. 21 is a view similar to FIG. 20 showing an even later stage in use of the FIG. 14 apparatus.

The next step is to proximally retract tube 350. This allows inside fingers 52c to spring radially out inside the side wall of the aorta 10 as shown in FIG. 20. A subsequent step is to shift tube 340 distally, which releases connector 50 from the circumferential restraint of the distal portion 346 of that tube. This allows connector 50 to resiliently fully enlarge to its final, relatively large circumference as shown in FIG. 21.

Figure 22:
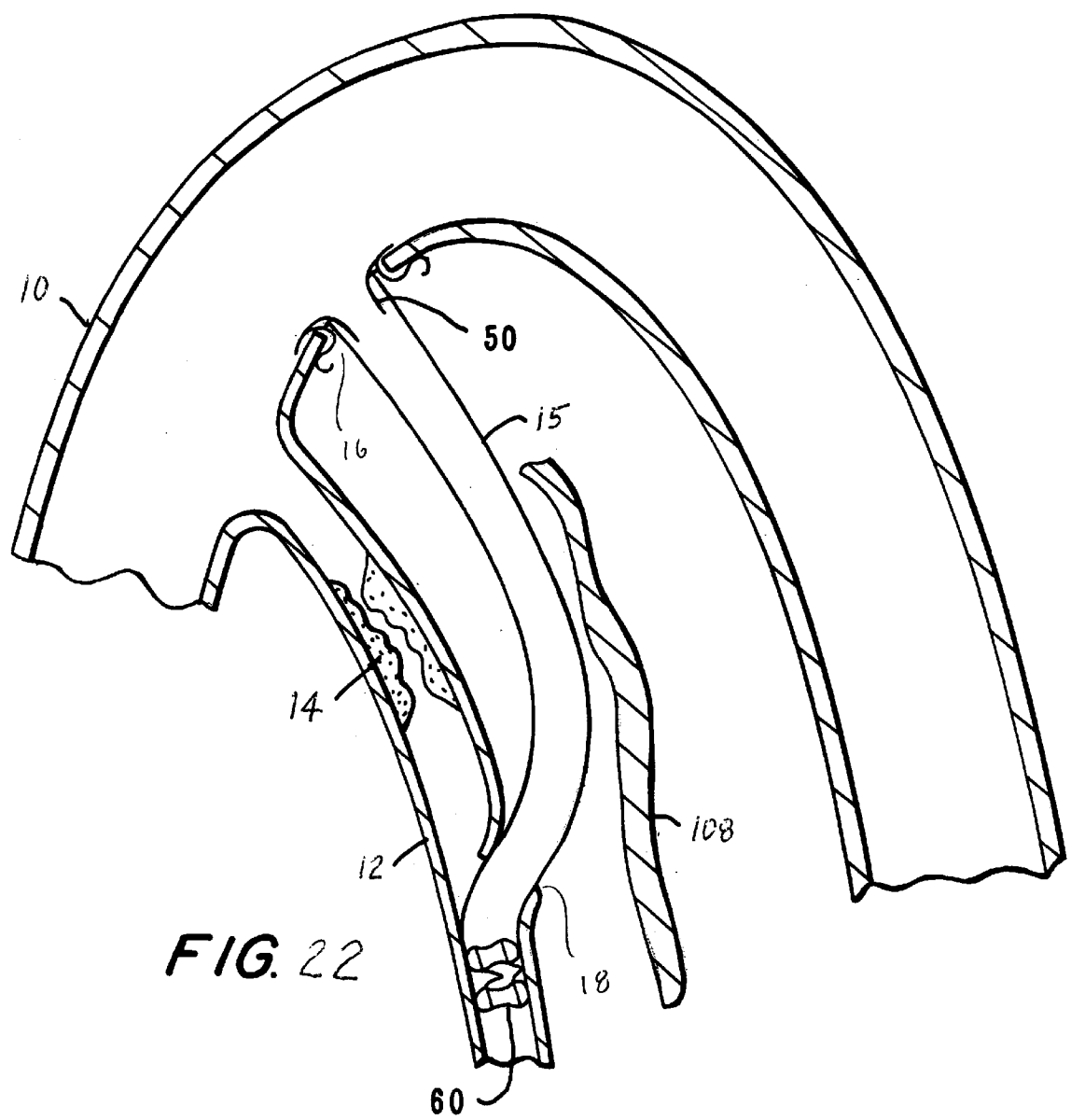
FIG. 22 is a view similar to FIG. 15 showing an illustrative end result of use of the apparatus and methods of this invention.
Figure 27:
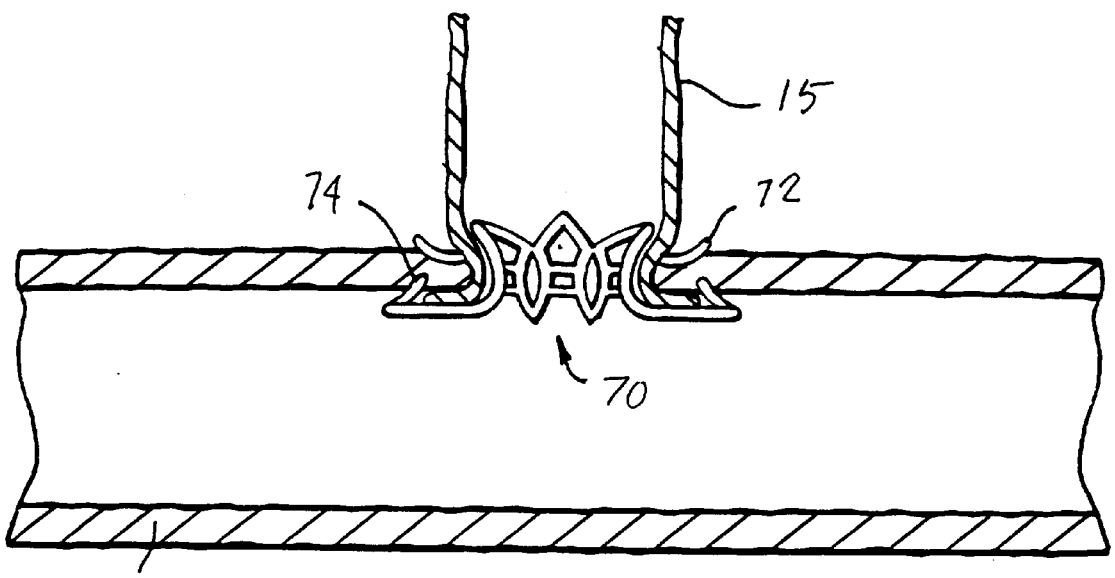
FIG. 27 is a view similar to FIG. 26 showing the end result of using the FIG. 23 apparatus in accordance with the invention.
Figure 28:
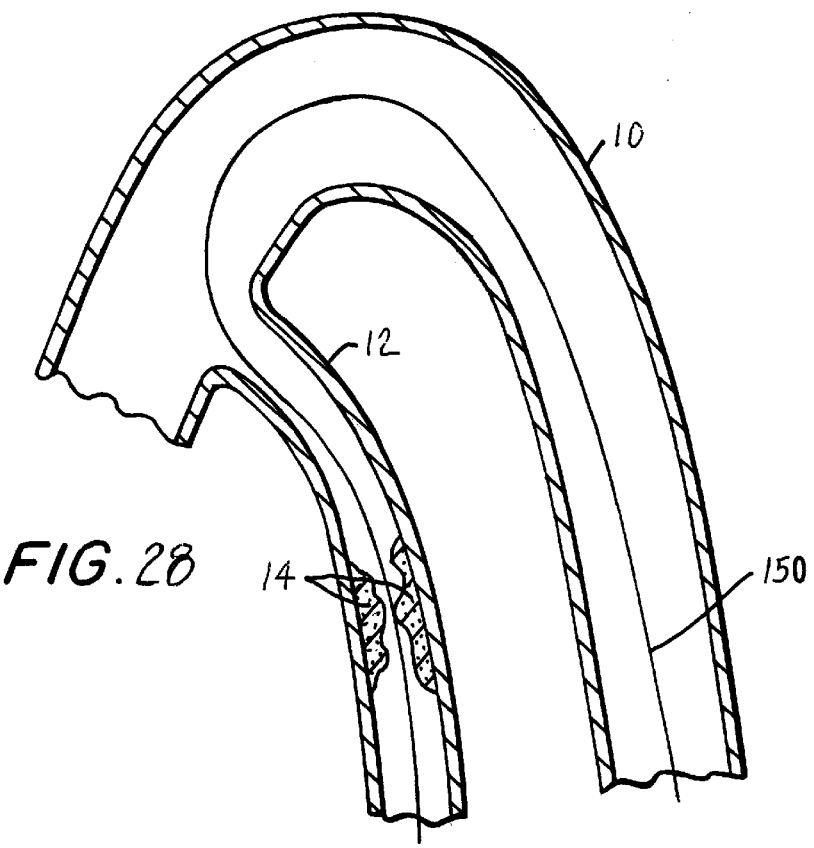
FIG. 28 is a simplified longitudinal view showing an early stage in use of illustrative apparatus and methods in accordance with an alternative embodiment of this invention.

All of structures 208, 210, and 300 can then be withdrawn proximally from the patient. This leaves the final condition of the patient as shown in FIG. 22, i.e., with connector 50 providing an anastomotic connection between the side wall of aorta 10 and the proximal end of graft conduit 15 at location 16, and with connector 60 providing an anastomotic connection between the distal end of graft conduit 15 and the inside of coronary artery 12 downstream from narrowing 14 at location 18. The downstream portion of coronary artery 12 is thereby supplied with aortic blood via bypass graft conduit 15. As much as possible of the work of installing graft 15 has been performed in a minimally invasive way, and in particular via lumens of the patient's circulatory system.

It will be noted that the present invention is suitable for adding a new length of graft conduit to a patient's circulatory system between two points on that system that can be quite widely spaced from one another (as in the case of the aorta, on the one hand, and a coronary artery beyond an narrowing, on the other hand). The graft is installed outside the patient's existing circulatory system through the space in the patient between the above-mentioned two endpoints. The graft is installed along a path initially defined by guide member 210.

In an alternative embodiment of the subject invention, an alternative connector apparatus, connector 70, may be used to make the connection between the graft 15 and the coronary artery 12 and the aorta 10. Connector 70 is substantially described in U.S. patent application Ser. No. 09/186,774, incorporated by reference, above. Connector 70 is formed in such a way that it is annularly enlargeable (e.g., by inflation of a balloon that is temporarily disposed inside the connector). It will be appreciated that as connector 70 annularly enlarges, it generally axially shortens. Graft conduit 15 is placed over connector 70 so that radially outwardly deflected members 72 penetrate and pass through the side wall of the graft conduit (e.g., as a result of compressing the graft against the fingers, thereby forcing the fingers to pierce through the graft wall). The sharpened free ends of members 72 facilitate penetration of conduit 15 by members 72. Connector 70 also includes a plurality of annularly spaced members 74 that in this case have free end portions that are deflectable radially out from the remainder of structure 70 as shown.

Illustrative apparatus 260 for delivering connector 70 and graft 15 to the distal anastomosis location 18, and for then deploying the connector and graft, is shown in FIG. 23. Apparatus 260 includes an optional guide wire 210, which may be installed, for example, as described above with respect to FIGS. 9–13. The remainder of the apparatus is then slid into the patient along guide wire 210. Alternatively, guide wire 210 may be omitted, or a leading guide member (e.g., a wire) may be fixedly mounted on the distal (leftward in FIG. 23) end of the remainder of the apparatus.

Apparatus 260 includes a gradually tapered distal nose portion or dilator 262 which extends annularly around a central, longitudinally extending, guide wire lumen 222. Distal nose portion 262 has a substantially conical outer surface with a cone angle A, which is preferably less than about 15° (e.g., in the range from about 5° to about 15°, more preferably in the range from about 5° to about 10°). Such gradual tapering of nose portion 262 is desirable to enable nose portion to gradually enlarge an aperture in a side wall of a body fluid conduit to which graft 15 is to be connected without snagging on that conduit side wall. This geometry allows optimal passage across a body conduit wall (e.g., a coronary artery wall as shown in FIG. 8 and described below) with minimal wall damage, with minimal force being required, and with no catching or snagging on the wall. Distal nose portion 262 may have cutting edges to further facilitate entry through a body fluid conduit side wall.

Distal nose portion 262 is connected to tube 266, which extends proximally from the nose portion annularly around guide wire 210. Thus the lumen of tube 266 constitutes a proximal continuation of guide wire lumen 264. Tube 266 may be made of stainless steel hypotube, which allows the depicted apparatus to be pushed or pulled axially along guide wire 210.

A proximal portion of distal nose portion 262 is hollowed out as indicated at 268 to receive balloon 270, connector 70, and a distal portion of graft 15 substantially coaxially around a medial portion of tube 266. For this arrangement balloon 270 is provided as a hollow annulus at or near the distal end of hollow tubular member 272. The side wall of tube 272 may include a separate lumen (not shown but conventional for balloon catheters) through which pressurized inflation fluid may be supplied from a proximal region of the apparatus to balloon 270. Elements 272 and 270 are slidable axially along the outer surface of tube 266. Insertion of elements 70, 270, and 15 (FIG. 6) into the annular recess 268 in distal nose portion 262 deflects the radially outer-most portions of members 72 back over graft 15 as shown in FIG. 7. Tube 274, disposed substantially coaxially around element 272 inside graft 15 so that its distal end bears against members 72, may be used to help load elements 70, 270, and 15 into recess 268, and also to hold connector 70 in place in recess 268 during delivery of the connector to the anastomosis site in the patient.

FIG. 8 shows a typical use of apparatus 260 to deliver graft 15 for connection to an aperture in a side wall of a patient's tubular body conduit 12 (e.g., a coronary artery requiring a bypass graft). Guide wire 210 is first installed through a small aperture in the side wall of the conduit. The natural elastic recoil of the conduit 12 side wall seals the aperture around the guide wire so that there is little or no body fluid (e.g., blood) leakage out of the conduit via the aperture. The tapered distal nose portion 262 of apparatus 260 is then gradually forced into the aperture (e.g., by using tube 266 to push portion 262 distally into the aperture) to dilate the aperture. The natural elastic recoil of the conduit 12 side wall tissue continues to keep the aperture sealed or substantially sealed around portion 262.

When distal nose portion 262 has been pushed far enough into the aperture in the-side wall of conduit 12 so that connector 70 is part way through the aperture, further distal motion of elements 70, 272, 270, and 15 can be stopped (e.g., by holding a proximal portion of element 272 stationary). Tube 274 is then pulled proximally out of the patient. Thereafter, distal nose portion 262 is pushed farther into conduit 12 (e.g., by continuing to push distally on a proximal portion of element 266). This causes distal nose portion 262 to separate from connector 70, thereby exposing the connector and leaving it in the aperture through the conduit 300 side wall as shown in FIG. 9.

Figure 10:
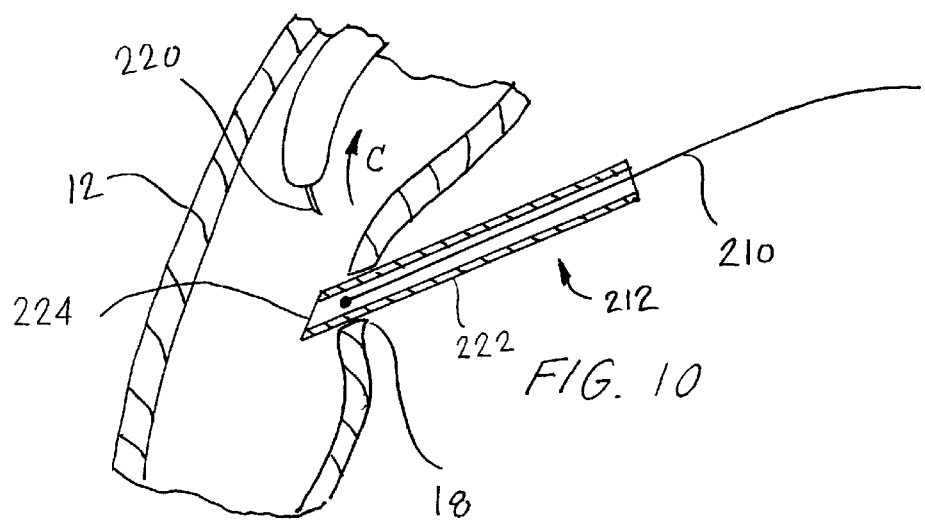
FIG. 10 is an enlarged sectional view, similar to FIG. 9, showing an early stage in the use of illustrative apparatus and methods in accordance with the invention.

The next step in use of apparatus 260 is to inflate balloon 270 as shown in FIG. 10. The balloon is typically sized to a specific anastomosis size (e.g., 3 millimeters diameter, 4 millimeters diameter, 20 etc.). Inflation of the balloon forces connector 70 to annularly enlarge and causing the extreme distal end of graft 15 to similarly flare out inside that side wall. This outward flaring of portions of connector 70 and graft 15 helps secure the connector and graft to the side wall of conduit 12, and also helps seal the graft to the conduit. The axial shortening of connector 70 that accompanies annular enlargement ensures that graft 15 is drawn into secure and fluid-tight engagement with conduit 12. The free ends of members 74 preferably penetrate the side wall of conduit 12 to further secure connector 70 and graft 15 in the aperture in the side wall. Members 74 may also flare out somewhat outside the side wall of graft 12 to help ensure that graft 15 remains open where it connects to conduit 12. Assuming that the connector is approximately properly positioned relative to the side wall of conduit 12 prior to inflation of balloon 270, the connector is effectively self-centering on the conduit 12 side wall as the balloon is inflated.

The next step in use of apparatus 260 is to deflate balloon 270 and withdraw all of elements 272, 270, 210, 262, and 266 (e.g., by pulling them proximally out of graft 15). This leaves the axial end portion of graft 15 connected to the side wall of conduit 12 by annularly enlarged connector 70 as shown in FIG. 11. In particular, in this example connector 70 provides an end-to-side anastomosis between graft 15 and conduit 12. Body fluid from graft 15 is able to flow into conduit 12 via this connection. Connector 70 presses graft 15 radially outward against the aperture through the side wall of conduit 12 all the way around that aperture, thereby preventing body fluid from leaking out of conduits 15 and 12. Connector 70 also prevents the end of conduit 15 from pulling out of the side wall of conduit 12.

According to an alternative embodiment of the subject invention, the elongated guide member is introduced into a lumen of the patient's circulatory system from a remote location, e.g., into the femoral artery at the leg, and advanced intraluminally to the anastomotic site.

Figure 33:
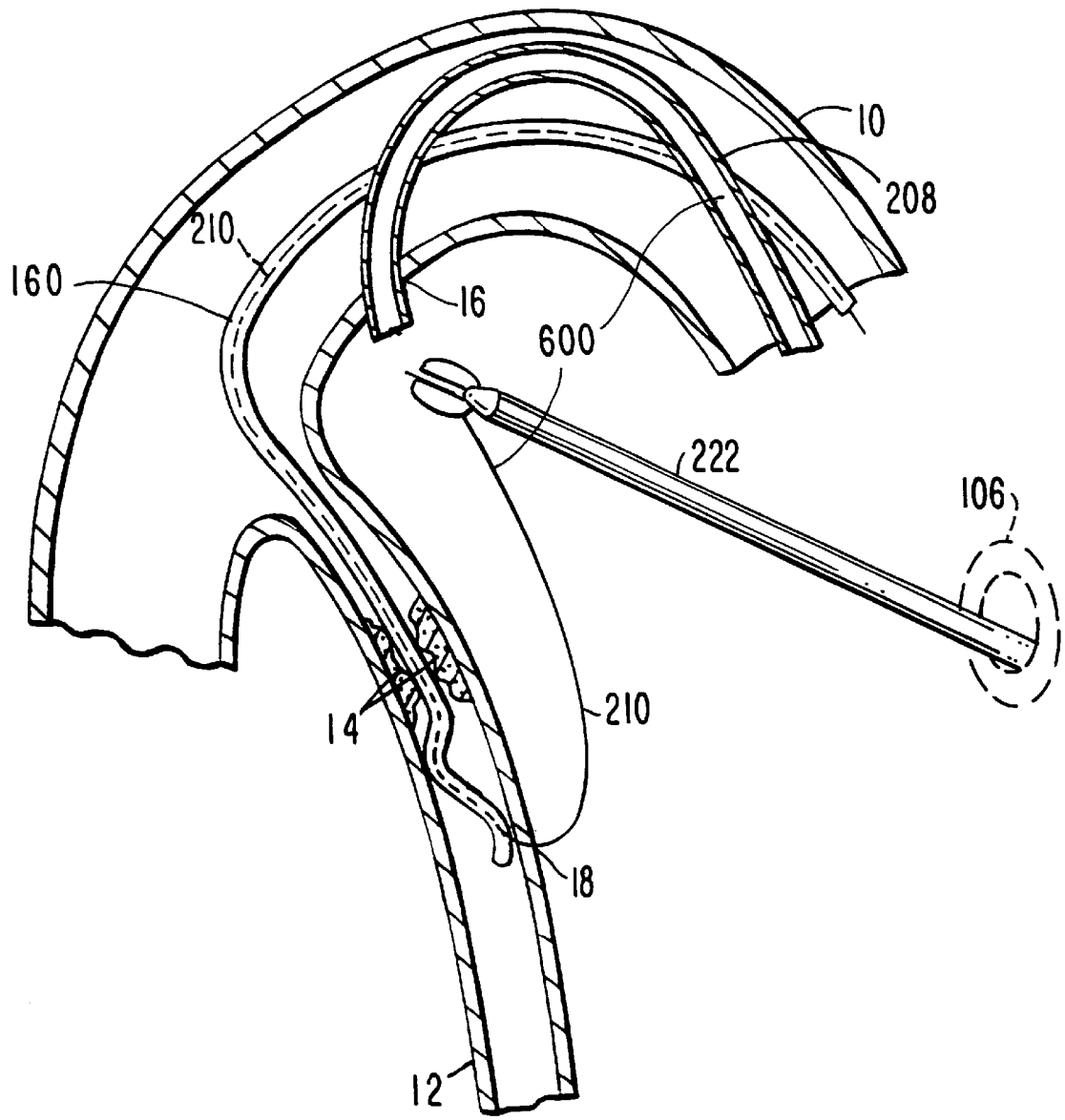
FIG. 33 is a simplified longitudinal view similar to FIG. 30, illustrating a later stage in use of illustrative apparatus and methods in accordance with the invention.

The elongated guide member is introduced into the patient's circulatory system and advanced past the narrowing of the coronary artery to the distal anastomosis site. Thus, this embodiment is advantageous when the narrowing permits some fluid flow, but is not a significant reduction or total occlusion of the vessel. The process of introducing the longitudinal guide wire in this manner is described in U.S. patent application Ser. No. 08/745,618 (293/002), filed Nov. 7, 1996, and Ser. No. 09/187,364 (293/036), filed Nov. 6, 1998, incorporated by reference above. As shown in FIG. 33, an early stage in an illustrative coronary artery bypass procedure in accordance with the invention includes introducing a longitudinal guide member 150 (typically a guide wire, and therefore sometimes referred to as such herein) into the patient's circulatory system across the coronary artery narrowing 14 to be bypassed.

Figure 29:
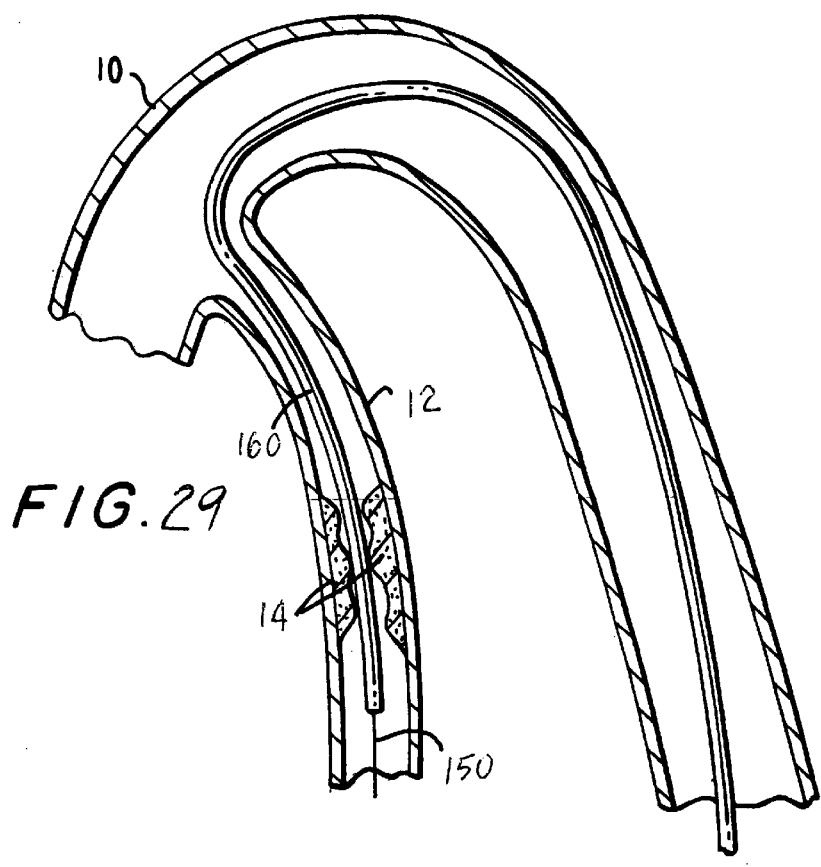
FIG. 29 is a view similar to FIG. 28 showing a later stage in use of illustrative apparatus and methods in accordance with the invention.

After guide member 150 is across narrowing 14 as shown in FIG. 29, a catheter or catheter-like structure 160 is introduced into the patient along guide member 150 as shown in FIG. 29. Guide wire 150 facilitates passage of the distal portion of catheter 160 through narrowing 14 as shown in FIG. 29. After the distal portion of catheter 160 has passed through narrowing 14 as shown in FIG. 29, guide wire 150 may pulled proximally out of the catheter 160 and out of the patient.

Figure 30:
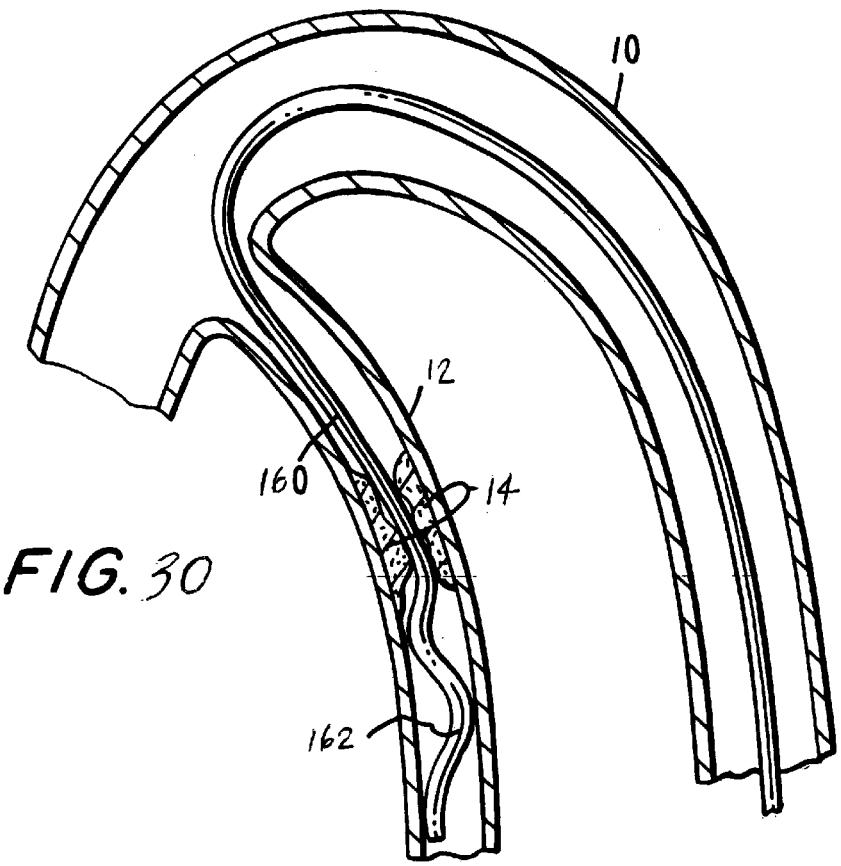
FIG. 30 is a view similar to FIG. 29 showing a still later stage in use of illustrative apparatus and methods in accordance with the invention.

A medial portion 162 of catheter 160 is preferably constructed to form a laterally extending arch as shown in FIG. 30 after guide wire 150 has been withdrawn from the catheter. For example, catheter 160 may be made so that it resiliently tends to form an arch of a predetermined lateral extent when it is freed from the straightening effect of guide wire 150.

Figure 31:
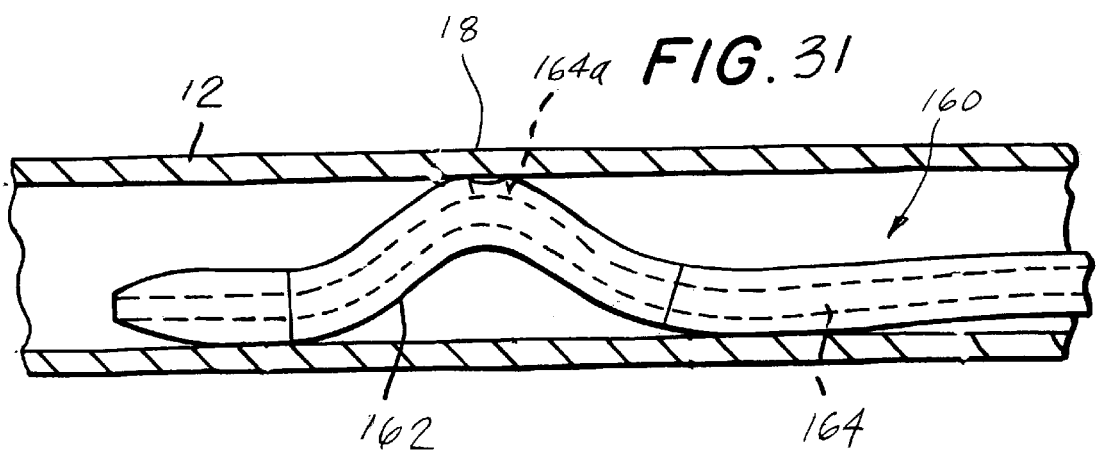
FIG. 31 is a simplified enlargement of a portion of FIG. 30, illustrated in section.

As illustrated in FIG. 31, the lumen 164 in catheter 160 has a side branch 164a which exits from the side wall of the catheter 160 at or near the apex of the above-described arch 162 in the catheter. A reinforcing layer such as a braid of wires may be included to enable the catheter to transmit torque and to provide kink resistance. A polymer layer (e.g., Pebax or nylon) provides support and curve retention. Internal lumen 164 preferably extends along the entire length of the catheter and is used to allow the catheter to track over guide wire 150 as described above, and to subsequently guide a longitudinal piercing structure to the point on the wall of artery 12 where it is desired to connect one end of a bypass graft, e.g., distal anastomosis location 18. (The piercing structure and its use will be described in more detail below.) The distal tip portion of catheter 160 may be made especially soft and/or the external surface of the catheter may be coated with polytetrafluoroethylene to enhance the ability of the catheter to pass through an narrowing, such as narrowing 14. A soft tip also helps make catheter 160 atraumatic. The distal tip portion of the catheter may be tapered in the distal direction for similar reasons.

As an alternative to having a medial portion 162 of catheter 160 arch as shown in FIGS. 30 and 31 when guide wire 150 is withdrawn from the catheter, a distal portion of the catheter may be configured to deflect or curve to the side when guide wire 150 is withdrawn as described in U.S. patent application Ser. No. 09/187,364 (293/036), or alternatively the distal end of the lumen within the catheter may be shaped to deflect the guide wire laterally, as described in U.S. patent application Ser. No. 08/745,618 (293/002), both incorporated by reference above. Further depiction and explanation of the invention will be made with reference to embodiments of the FIG. 31 type, but it will be understood that embodiments described above can e used instead if desired.

In an early step in the invention, catheter 160 may be positioned within the vessels first. More particularly, catheter 160 may be intraluminally advanced as described above (see, FIG. 30), and aortic access catheter 208 subsequently installed (see, FIG. 8). It is also understood that aortic access catheter 208 may be installed in the patient first, and catheter 260 subsequently positioned in the coronary artery 12. Alternatively, catheter 160 and aortic access catheter 208 may be simultaneously positioned. A further step is the provision of a surgical access opening in the patient's chest adjacent the two anastomosis sites, as described above with respect to FIGS. 2–2a.

Figure 32:
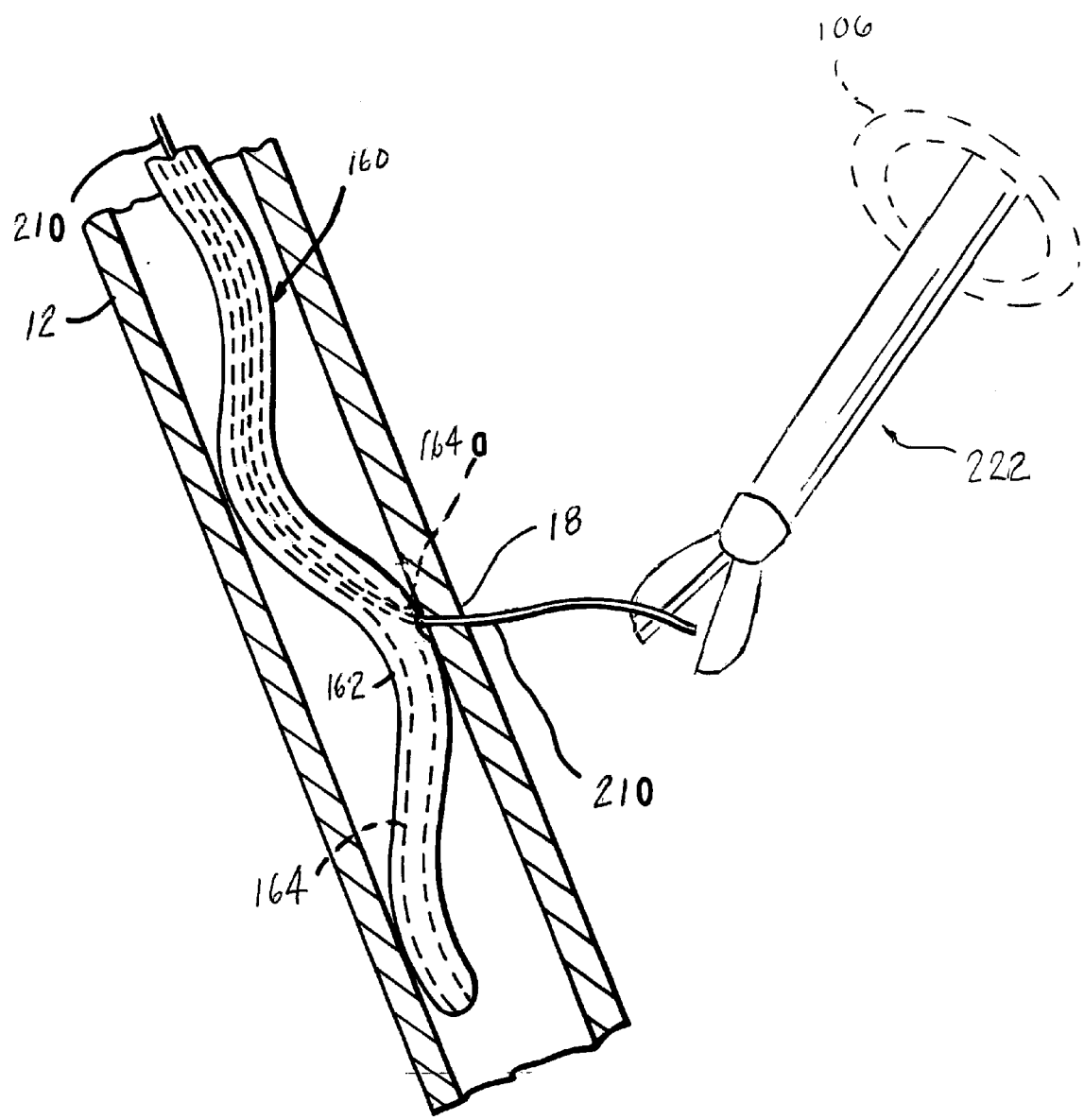
FIG. 32 is a sectional view similar to FIG. 31, illustrating a later stage in use of illustrative and methods and additional apparatus, in accordance with the invention.

As illustrated in FIG. 32, a subsequent step involves inserting an elongated piercing structure, which may be elongated guide member 210, (e.g., primarily a metal wire or wire-like structure) into catheter 160 along the lumen 164 formerly used for guide wire 150. Because catheter portion 162 is now arched as shown in FIG. 32, the distal end of piercing structure 210 tends to follow lumen branch 164a out of catheter 160 and into contact with the interior surface of the side wall of coronary artery 12. The distal tip of piercing structure 210 is sufficiently sharp and structure 210 is sufficiently stiff that the distal tip of structure 210 can be pushed out through the coronary artery wall tissue at the desired location, e.g., distal anastomosis location 18.

A surgical grasping apparatus 222, substantially similar to apparatus 214, described above with respect to FIG. 9, is inserted through the surgical access opening 106 to a position near the coronary artery 12 where structure 210 has pierced the coronary artery wall. Structure 210 is grasped by surgical instrumentation 222.

As illustrated in FIG. 33, surgical apparatus 222 holds guide member 210 and moves it to the distal opening of aortic access catheter 208. This movement may be assisted by simultaneously advancing guide member 210 along the patient's circulatory system at the same rate in which apparatus 222 advances the distal end to aortic access catheter 208. Surgical apparatus 222 may be substituted with other apparatus known in the art, such as hooks or snares, e.g., as described in application Ser. No. 09/187,364 (293/036) and Ser. No. 08/745,618 (293/002). Moreover, if there is sufficient access, the physician may manually grasp guide member 210 and convey it to aortic access catheter 208.

It is contemplated that the graft may be inserted over the guide structure 600 at this time, as will be described in greater detail below.

Guide member 210 is inserted inside aortic access catheter 208, and advanced further into and along the lumen thereof. This may be assisted by surgical apparatus 222. Structure 210 is advanced along the lumen of catheter 208, at least until an end portion thereof exits the patient at the remote location, i.e., the leg. The condition of the relevant portion of the patient and the apparatus after these operations may be shown in FIG. 34.

Figure 34:
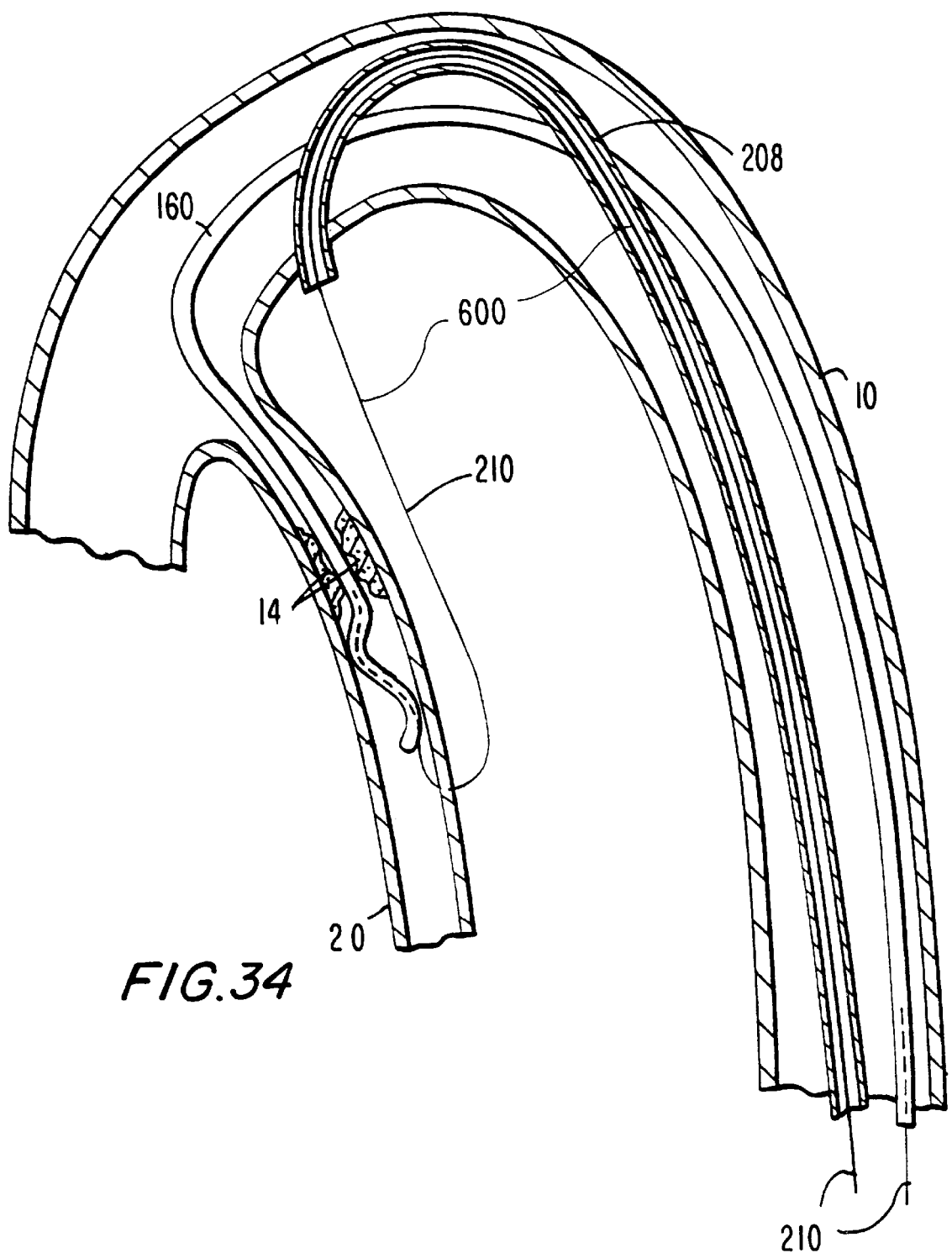
FIG. 34 is a simplified longitudinal view similar to FIG. 33, illustrating a still later stage in use of illustrative apparatus and methods in accordance with the invention.
Figure 35:
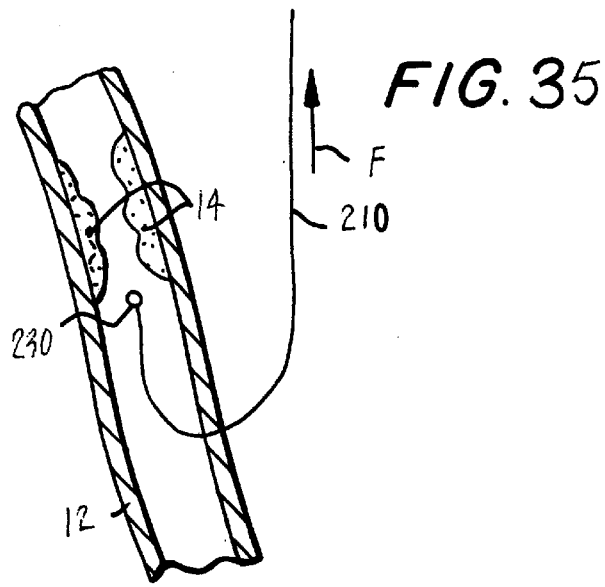
FIG. 35 is a view similar to a portion of FIG. 34 showing another illustrative embodiment of apparatus and methods in accordance with the invention.
Figure 36:
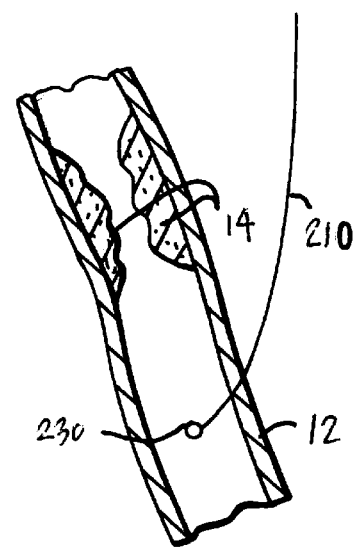
FIG. 36 is a view similar to FIG. 35 showing a later stage in use of the FIG. 35 apparatus.
Figure 37:
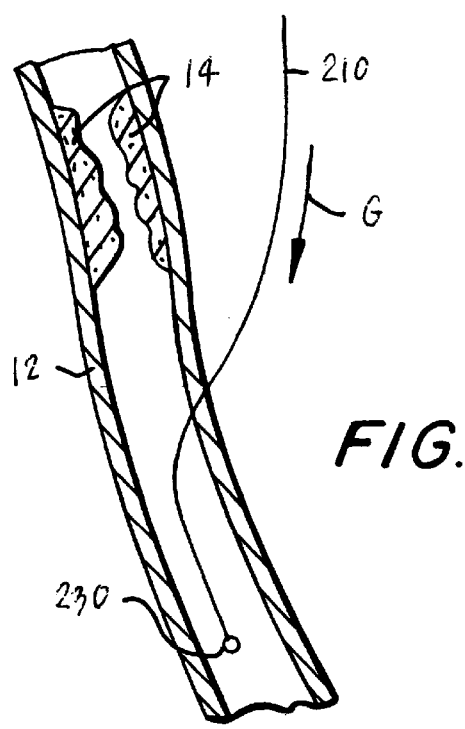
FIG. 37 is a view similar to FIG. 35 showing a still later stage in use of the FIG. 35 apparatus.
Figure 38:
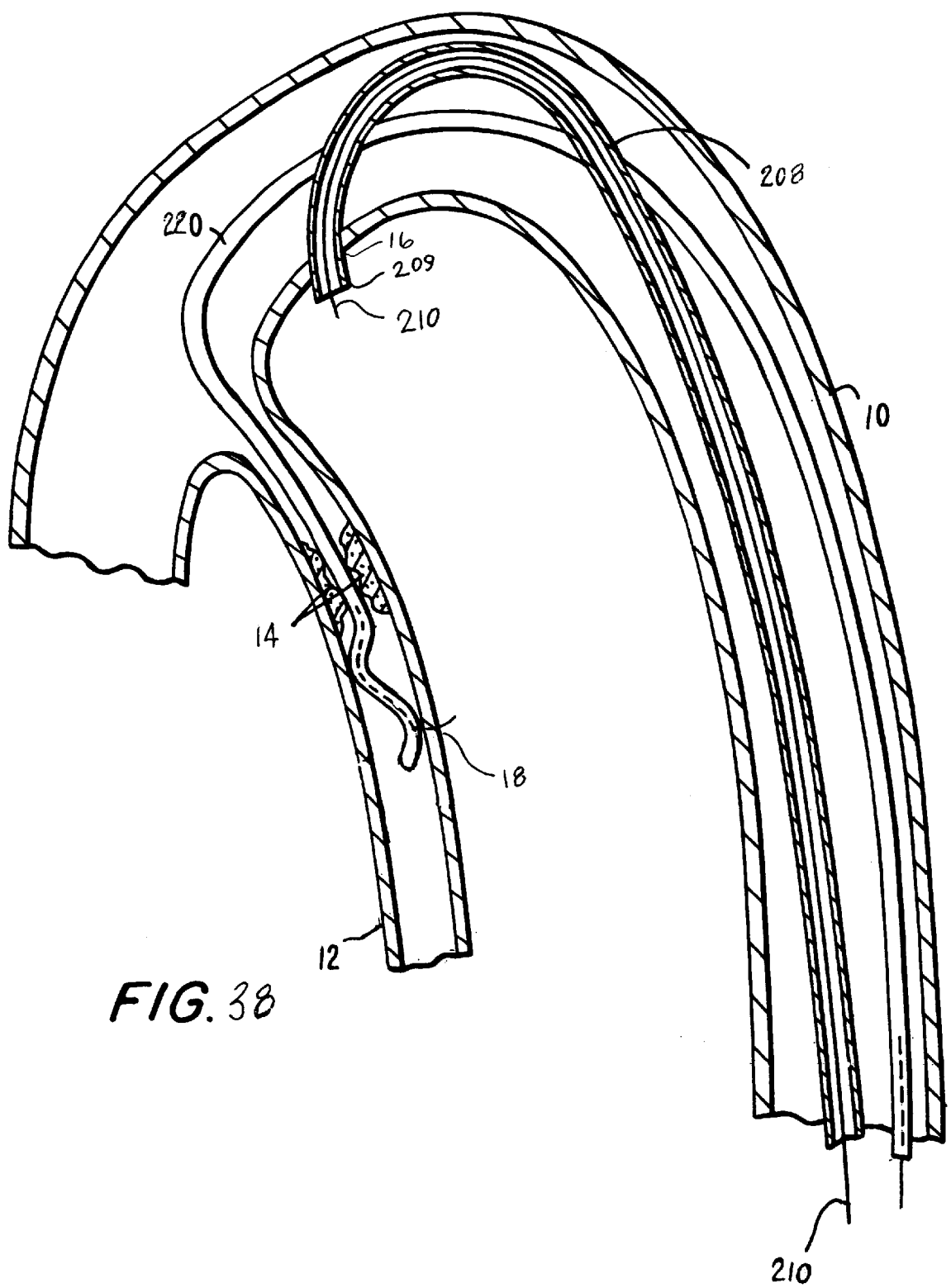
FIG. 38 is a simplified longitudinal view showing an early stage in use of illustrative apparatus and methods in accordance with another alternative embodiment of this invention.
Figure 39:
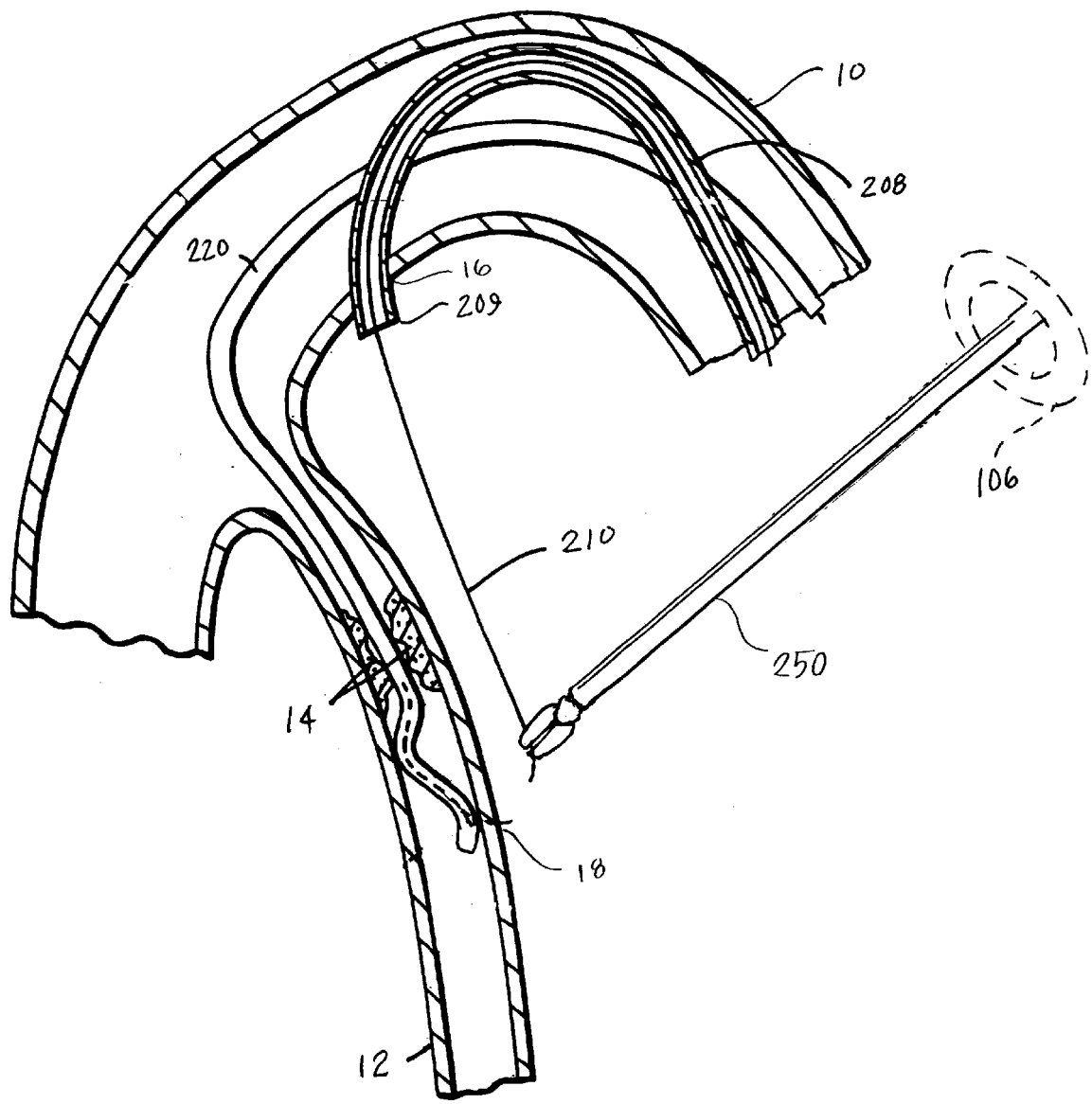
FIG. 39 is a view similar to FIG. 38 showing a later stage in use of illustrative apparatus and methods, and additional apparatus, in accordance with this invention.

It may be desired that the portion of guide member 210 extend downstream in coronary artery 12. However, as illustrated in FIG. 34, guide member 210 at least initially extends through coronary artery 12 and aorta 10. Guide member is withdrawn in direction F (FIG. 35), at least until an end portion 222 of guide member 210 is positioned downstream of narrowing 14. The steps of repositioning guide member 210 from an upstream position (FIG. 35) to the downstream position (FIG. 32) is described in greater detail in application Ser. No. 09/187,364 (293/036) and Ser. No. 09/187,361 (293/038), incorporated by reference above. As illustrated in FIG. 35, guide member 210 is provided with an atraumatic end portion 266. Guide member 210 is withdrawn from the coronary artery 12, e.g., in direction indicated by arrow F, to the configuration shown in FIG. 31. Guide member 210 is permitted to resume a straightened configuration. As shown in FIG. 32, guide member 210 is re-inserted into the coronary artery 12, as indicated by arrow G. This causes end portion 266 to move in the downstream direction along the coronary artery lumen.

After the guide wire has been positioned between the two anastomotic sites, the graft may be delivered over guide wire to the desired location and connected to the aorta and the coronary artery as described above with respect to FIGS. 14–22.

According to another alternative embodiment, the aortic access catheter 208 is positioned across an aperture in the aorta, or other vessel, as described above (FIGS. 3–8). Subsequently, the elongated guide member 210 is inserted into the aortic access catheter 208 and advanced along the catheter at least until the guide member 210 is adjacent the distal opening 209 of the catheter (FIG. 33).

A subsequent step may be to clearly indicate the distal anastomosis location 18 for the physician to insert the guide member 210 into the coronary artery 12, or other vessel and then to move the guide member 210 to that location. A device, such as marker wire 220 having radiologic properties, as described above with respect to FIG. 9, may be inserted along the coronary artery 12 to provide a visual cue of the desired location.

As illustrated in FIG. 34, the end of the guide wire 210 may then be grasped with surgical apparatus, such as apparatus 250, which may be inserted through the surgical access opening to the anastomotic site, as described above. Apparatus 250 may be used to convey the end portion of guide member 210 to the distal anastomosis location 18. Assistance to the process of moving the guide member 210 to the distal anastomotic location 18 may be provided by pushing guide member 210 out of the aortic access catheter 208 at the same rate as the distal end of the guide member is moved by the surgical instrumentation 250. It is understood that the distal end of guide member may be moved by other instrumentation known in the art, or manually by the physician if there is sufficient access.

A next step may be the insertion of guide member 210 into the coronary artery 12 in a similar manner to that described with respect to FIGS. 9–12, above. A cannula needle, such as cannula needle 212, may be used to pierce the coronary artery at the distal location. According to one embodiment, the cannula needle 212 is positioned coaxially surrounding the distal end of guide wire 210. As illustrated in FIG. 10, the distal tip portion 224 of the cannula needle 212 passes through the wall of the coronary artery 12, and the distal end of the guide member 210 is subsequently advanced into the coronary artery (FIG. 11). In another embodiment, the cannula needle may be provided with a longitudinal notch (not shown), such that the cannula needle has a substantially "C"-shaped cross-section to permit the cannula needle 212 to be removed after both ends of the guide wire 210 are in position. According to an alternative embodiment of the above method, cannula needle 212 may pierce the coronary artery first, and then is removed from the coronary artery. Subsequently, guide member 210 is advanced through the wall of the coronary artery 12 at the location pierced by the cannula needle 212. The distal end portion of the guide wire is positioned downstream within the coronary artery as described with respect to FIG. 12, above.

After the guide wire 210 has been positioned between the two anastomotic sites 16 and 18, the graft may be delivered over guide wire to the desired location and connected to the aorta and the coronary artery as described above with respect to FIGS. 14–22.

In another alternative embodiment, the graft conduit 15 is introduced through the surgical access opening 106 described above (See, e.g., FIGS. 2–2a), rather than intraluminally along and through a tubular conduit, such as aortic access catheter 208 (See, e.g., FIGS. 15–22). Under certain circumstances, surgical introduction of one or more grafts may be preferred. For example, coronary artery bypass procedure may require the attachment of several grafts to the patient's heart. In such a case, it may be indicated that one or more graft sections be introduced intraluminally, as described above, and that one or more graft sections be introduced surgically as will be described in greater detail, below. Under other circumstances, it may be advantageous to introduce the graft surgically, if the diameter, length, elastic characteristics, or other features of the graft suggest that intraluminal insertion within another tubular body conduit may be less desirable.

According to an early stage in this embodiment, the aortic access catheter 208 is positioned across an aperture in the aorta, or other vessel, as described above (FIGS. 3–8). Subsequently, the elongated guide member 210 is inserted into and along the patient's tubular body structure. For example, the guide member 210 may be advanced along and through the aortic access catheter 208 at least until an end portion of the guide member 210 is adjacent the distal opening of the catheter (See, e.g., FIG. 33).

Figure 40:
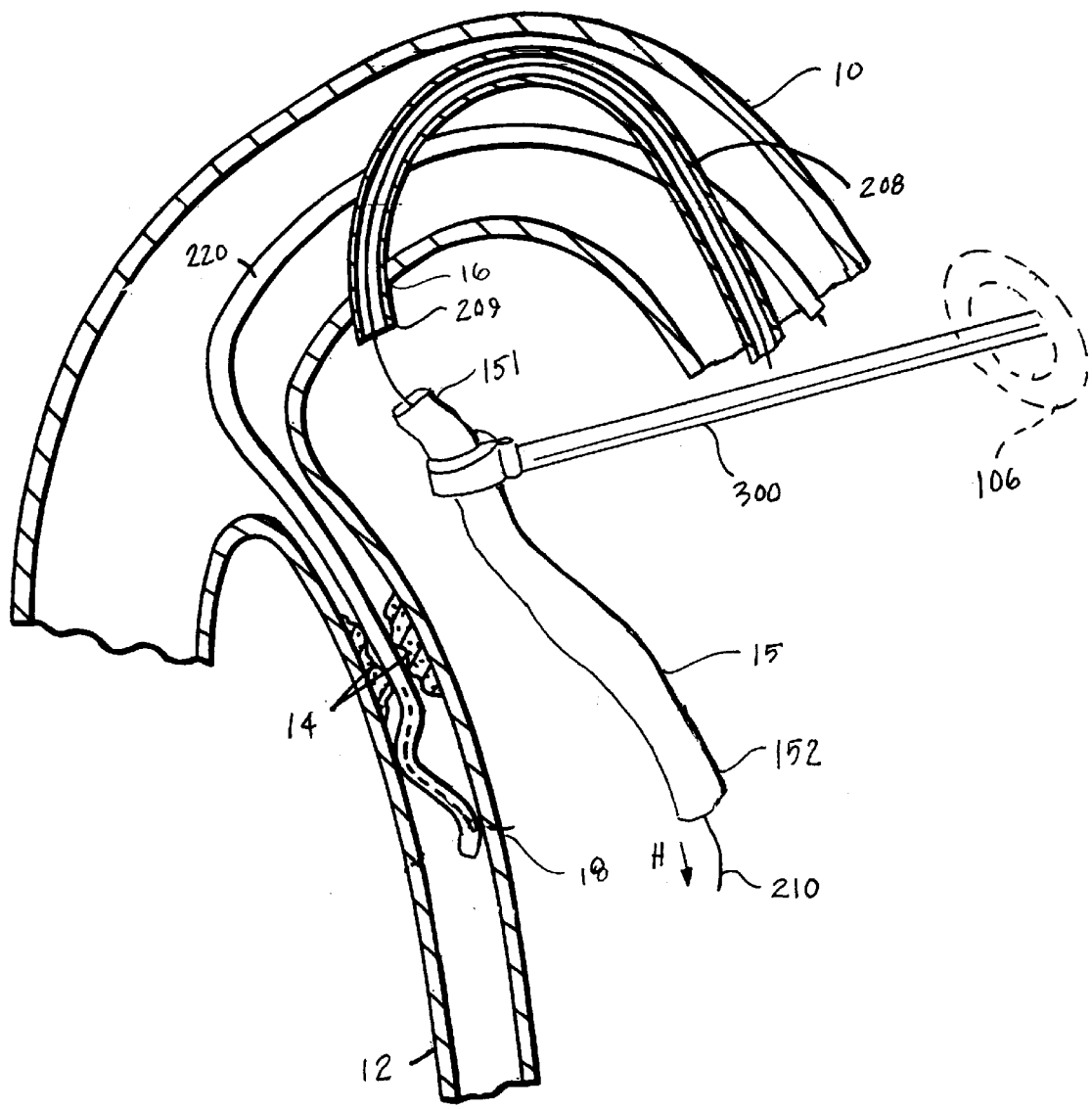
FIG. 40 is a view similar to FIG. 39 showing a later stage in use of illustrative apparatus and methods, and additional apparatus, in accordance with this invention.

A next step in the procedure may be to introduce the graft 15 to the patient's body cavity adjacent the anastomosis locations 16 and 18. Graft conduit 15 is inserted through the surgical access opening 106. As illustrated in FIG. 40, surgical instrumentation, such as surgical apparatus 300, may be inserted through the surgical access opening to assist placing the graft conduit 15 over the guide member 210. Surgical apparatus 300 may be used to insert the first end portion 151 of the graft conduit 15 over the distal end portion of guide member 210. As surgical apparatus 300 maintains the graft conduit 15 in place, guide member 210 is advanced distally within graft conduit 15 as shown by arrow H in FIG. 40, at least until the distal end portion thereof protrudes from the second end portion 152 of the graft conduit 15. The distal end portion of the guide member 210 may subsequently be installed in the coronary artery 12 through the use of surgical instrumentation, such as cannula needle 212 described with respect to FIGS. 9–12.

The graft may be attached to the patient's vessels, such as the coronary artery and the aorta. For example, one end portion 151 of graft 15 is moved to the proximal anastomosis site 16, with surgical instrumentation, such as instrument 300, having an atraumatic surface to minimize damage to the graft tissue.

Figure 41:
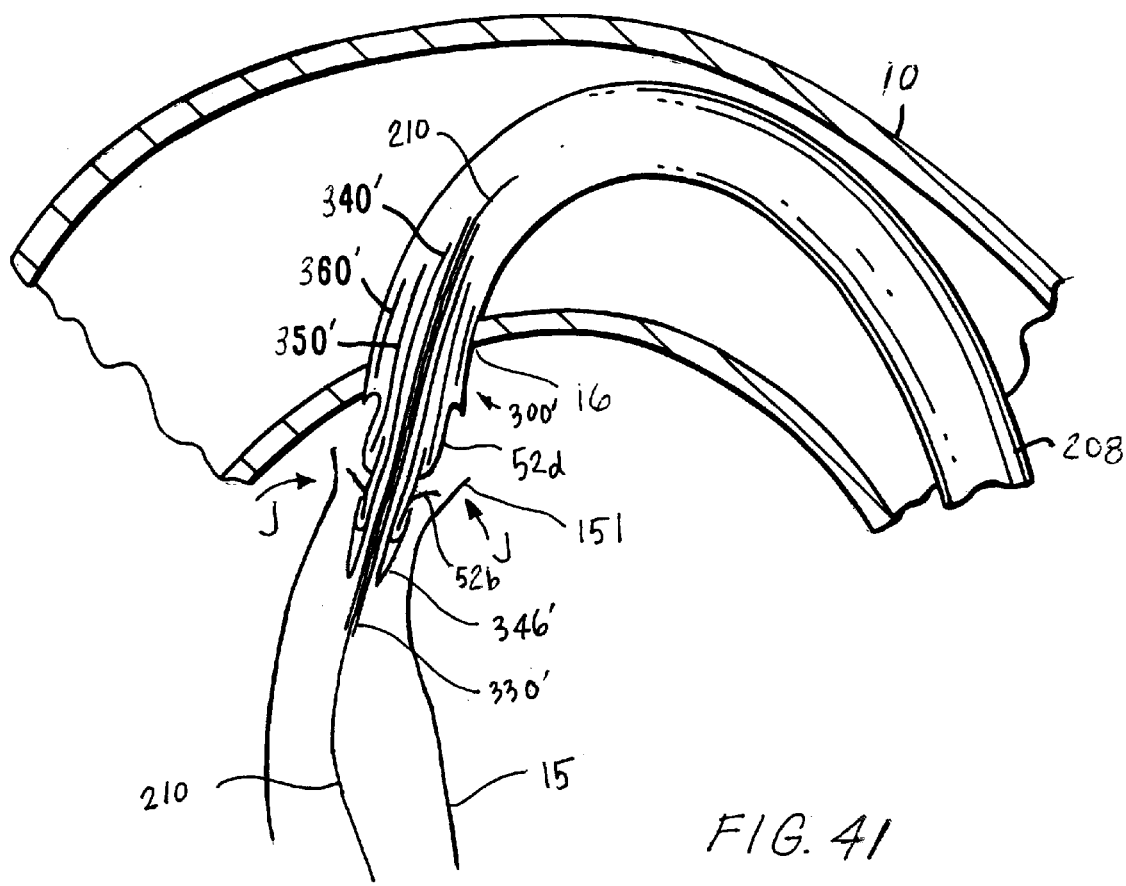
FIG. 41 is an enlarged view similar to FIG. 40, but with more elements shown in section, and showing a later stage in use of illustrative apparatus and methods in accordance with the invention.

The connection to the aorta is made by suturing, or by installing one of the connectors described hereinabove. As illustrated in FIG. 41, apparatus 300', similar to apparatus 300 described above with respect to FIG. 14, is inserted into and along aortic access catheter 208 to the proximal anastomosis site. Apparatus 300' is substantially similar to apparatus 300 in that apparatus 300' is provided with parts 346', 350', 360' and 340' for holding connector 50 in position. Apparatus 300' is deployed from aortic access catheter at least until graft retention fingers 52b are exposed. Surgical instrumentation (not shown) may be used to position end portion 151 of graft 15 adjacent graft retention fingers 52b. End portion 151 is attached to graft retention fingers 52b in direction illustrated by arrows J by surgical instrumentation. Connector 50 is deployed to connect graft 15 to aorta 10, substantially as described with respect to FIGS. 18–21.

The other end of the graft is moved to the distal anastomosis site, preferably using surgical apparatus, such as surgical apparatus 300. Connection to the coronary artery is achieved by suturing, or by installing one of the connectors, such as connector 60, described above.

According to another alternative embodiment of the invention, surgical assistance is provided to position the graft 15 adjacent the distal anastomosis location 18 and attach the graft 15 and the coronary artery 12, or other vessel. In this embodiment, the use of a guide member, previously described as guide member 210, for example, may be optionally omitted from the procedure.

Figure 42:
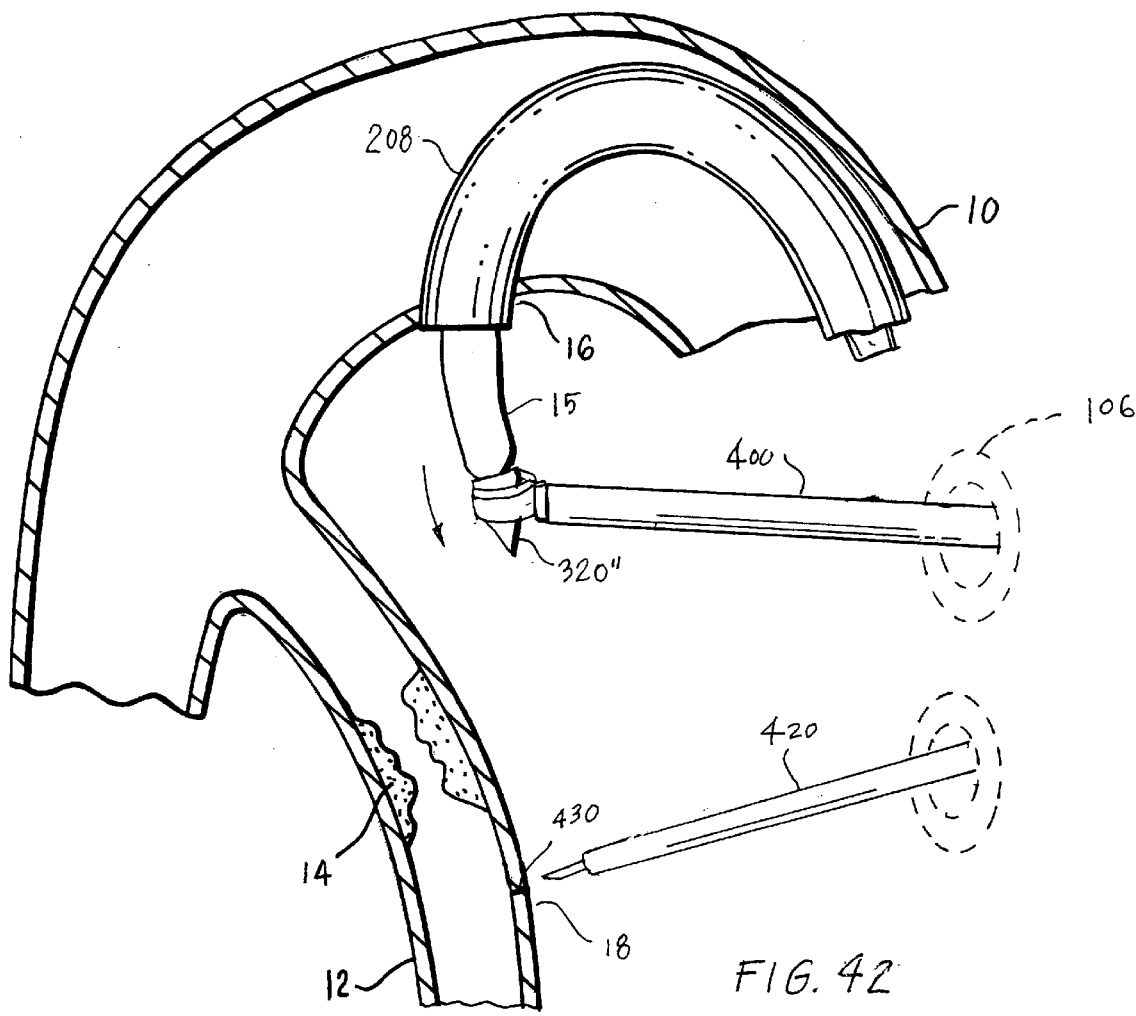
FIG. 42 is a simplified longitudinal view showing an early stage in use of illustrative apparatus and methods in accordance with still another alternative embodiment of this invention.

The aortic access catheter 208 is positioned across the aperture in the aorta 10, or other vessel, as described above (FIGS. 3–8). The graft 15 is subsequently inserted and passed into and along the patient's vascular system, or more particularly, along the aortic access catheter 208 to the proximal anastomosis location 16 (FIG. 42). Preferably, graft 15 is mounted within apparatus 300", which is substantially identical to assembly 300 described hereinabove with respect to FIG. 14. However, apparatus 300" omits a provision for a guide member, such as guide member 210 described above, to move coaxially therethrough. Distal tip structure 320", which is substantially identical to distal tip structure 320, is remotely intraluminally deployed beyond the end of the catheter 208.

Where there is limited access, a viewing scope, such as viewing scope 306 described above with respect to FIG. 9, may be inserted to assist in viewing the procedure. Surgical apparatus 400 (substantially similar to surgical apparatus 300 described with respect to FIG. 40) is inserted into the surgical access opening 160 to grasp and move the distal end portion of assembly 300", and more particularly tip structure 320", adjacent location 18 on coronary artery 12. A surgically introduced cutting instrument, such as scalpel 420, may used to make a small incision 430 in the coronary artery 20 at location 18.

Figure 43:
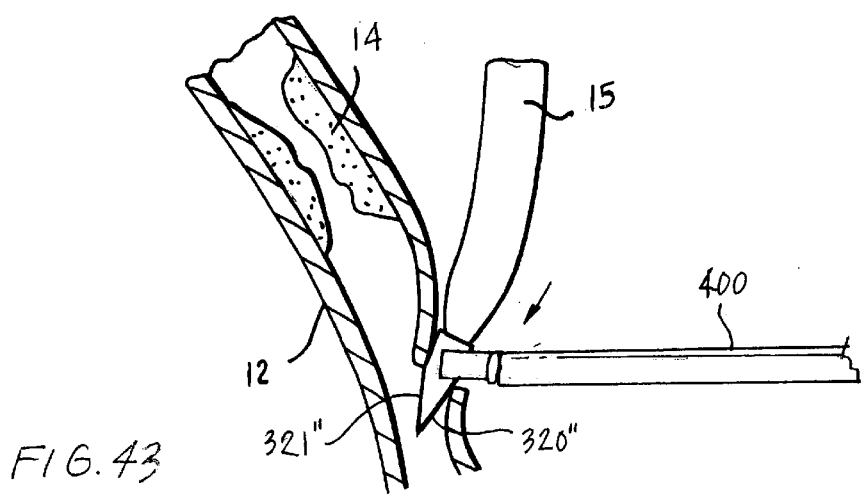
FIG. 43 is a view similar to a portion of FIG. 42 showing a later stage in use of illustrative apparatus and methods in accordance with the invention.

Tip structure 320" is then placed against the incision 430 in the coronary artery 12 by surgical apparatus 400. Tip structure 320" is passed through the coronary artery wall, as illustrated in FIG. 43. Alternatively, tip structure may be provided with a cutting structure, such as a sharpened tip portion (not shown), to pierce the coronary artery. Tip structure 320" may have a narrow tapered structure, such as a cone structure 321", to facilitate entry into the coronary artery 12 by gradually enlarging the opening as the tapered structure is advanced into the coronary artery.

Once the distal tip structure 320" has been satisfactorily inserted into the coronary artery, the grasper 400, and any other surgical apparatus used, may be removed from the operative site through the surgical access opening(s) in the patient's chest. The remainder of the anastomosis procedure may be carried out as described above with respect to FIGS. 17–22.

One alternative embodiment is a modification to the procedure described above with respect to FIGS. 15–17. According to this alternative embodiment, a graft 15 is not used to provide the bypass around the narrowing 14 in the coronary artery 12. Instead, a vessel, such as the internal mammary artery, is relocated to the coronary artery downstream of the narrowing in order to serve as an arterial blood source. Briefly, this procedure involves providing an annular cut in the IMA to form a free end, deploying an elongated guide member from the IMA, installing the elongated guide member in an aperture in the side wall of the coronary artery, shifting the free end of the IMA to the coronary artery using the elongated guide member to guide the IMA, and attaching the IMA to the coronary artery.

An early step in this procedure is to provide an annular cut in the IMA to form a free end. An intraluminal procedure for providing the annular cut and for dissecting the cut end from the surrounding tissue is described in Sullivan U.S. patent application Ser. No. 08/869,808 (293/016), incorporated by reference above, (with particular reference to FIGS. 3–6).

Figure 44:
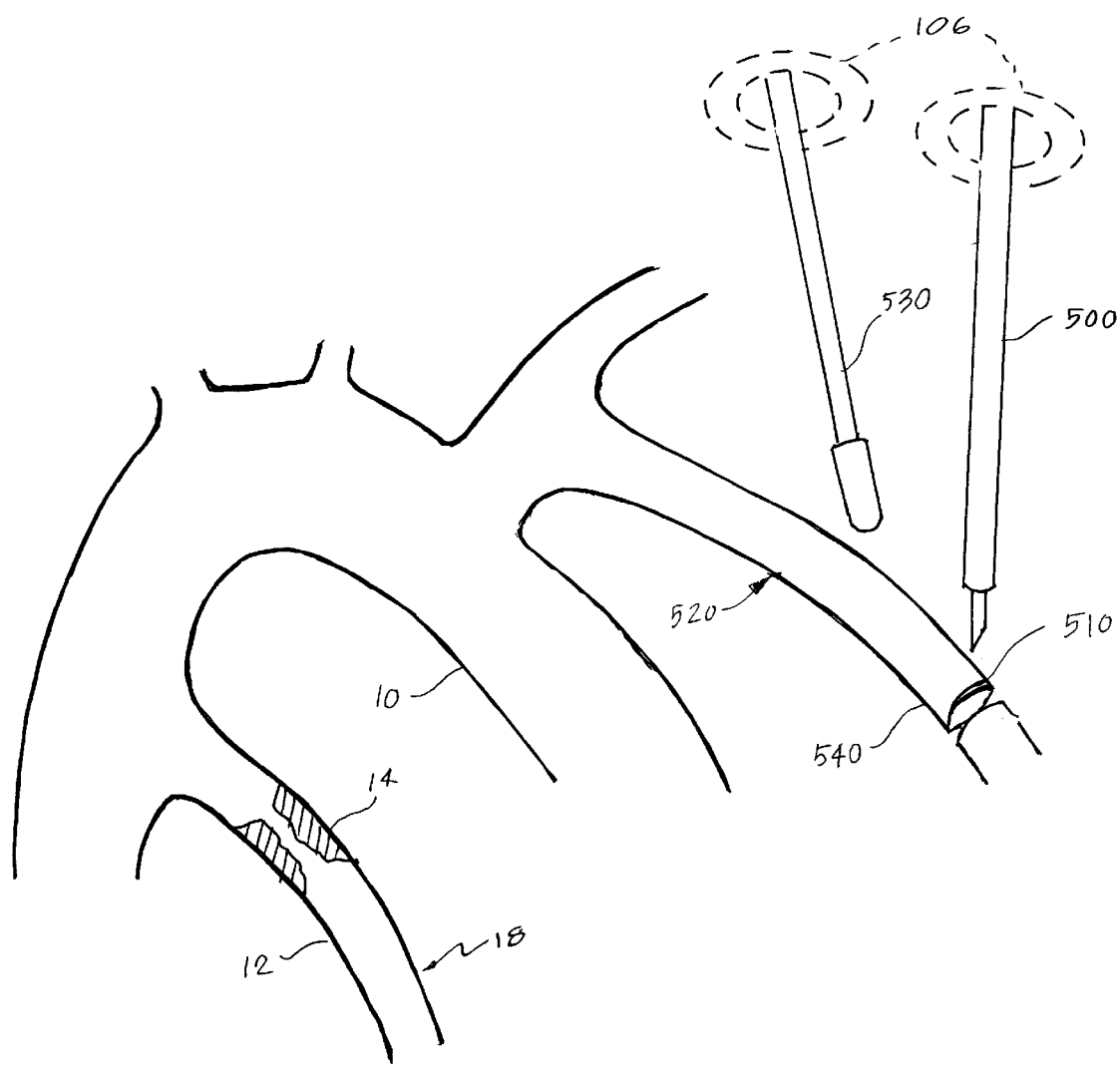
FIG. 44 is a simplified longitudinal view showing an early stage in use of illustrative apparatus and methods in accordance with another alternative embodiment of this invention.

According to the preferred embodiment of the invention, surgical assistance may be provided to provide the annular cut in the IMA. For example, a surgical instrument, such as cutting tool 500, may be inserted through the surgical access opening 106 to make the incision 510 in the IMA 520 (FIG. 44). A combination of dissection instruments, such as cutting tool 500, and blunt dissection instruments, such as blunt dissection tool 530 may be used to dissect the IMA 520 from the surrounding tissue. The annular incision 510 in the IMA forms a free end 540 from which a guide member 210 may be deployed.

FIG. 33, above, illustrates the deployment of the guide member 210 from a vessel, and FIG. 34, above, illustrates the movement of guide member 210 from the vessel to the distal anastomosis location 18 by grasping apparatus, such as apparatus 250. According to the alternative embodiment, this procedure is substantially the same as that described with respect to FIGS. 33–34, above, with certain modifications. Elongated guide member 210 is deployed along and through the patient's circulatory system until the end portion thereof extends from the free end portion 540 of the IMA 520. Surgical apparatus, similar to surgical apparatus 250, is used to advance the guide member 210 to the distal anastomosis location 18. The guide member 210 subsequently is passed through the coronary artery 12 and installed therein, as described above with respect to FIGS. 9–12, above.

A connector, such as one of the connectors described in applications Ser. No. 09/187,361 (293/038) or Ser. No. 09/186,774 (293/039), is attached to the end portion 540 of the IMA 520. For example, connector 60 described above, would be useful in making the anastomosis. Connector 60 may be introduced surgically by a surgical access opening, such as surgical access opening 106 in the patient and positioned at the end portion 540. Alternatively, component 60 may be introduced intraluminally through the patient's circulatory system to the end portion 540. Sutures may be applied to secure component 60 to the IMA 520 through the surgical access. Alternatively, connector 60 may be provided with fingers 62, which extend radially out from the main portion of connector 60 in order to pass through the free end portion 540 of IMA 520 and thereby secure the IMA to the connector. (See, FIGS. 14).

Figure 45:
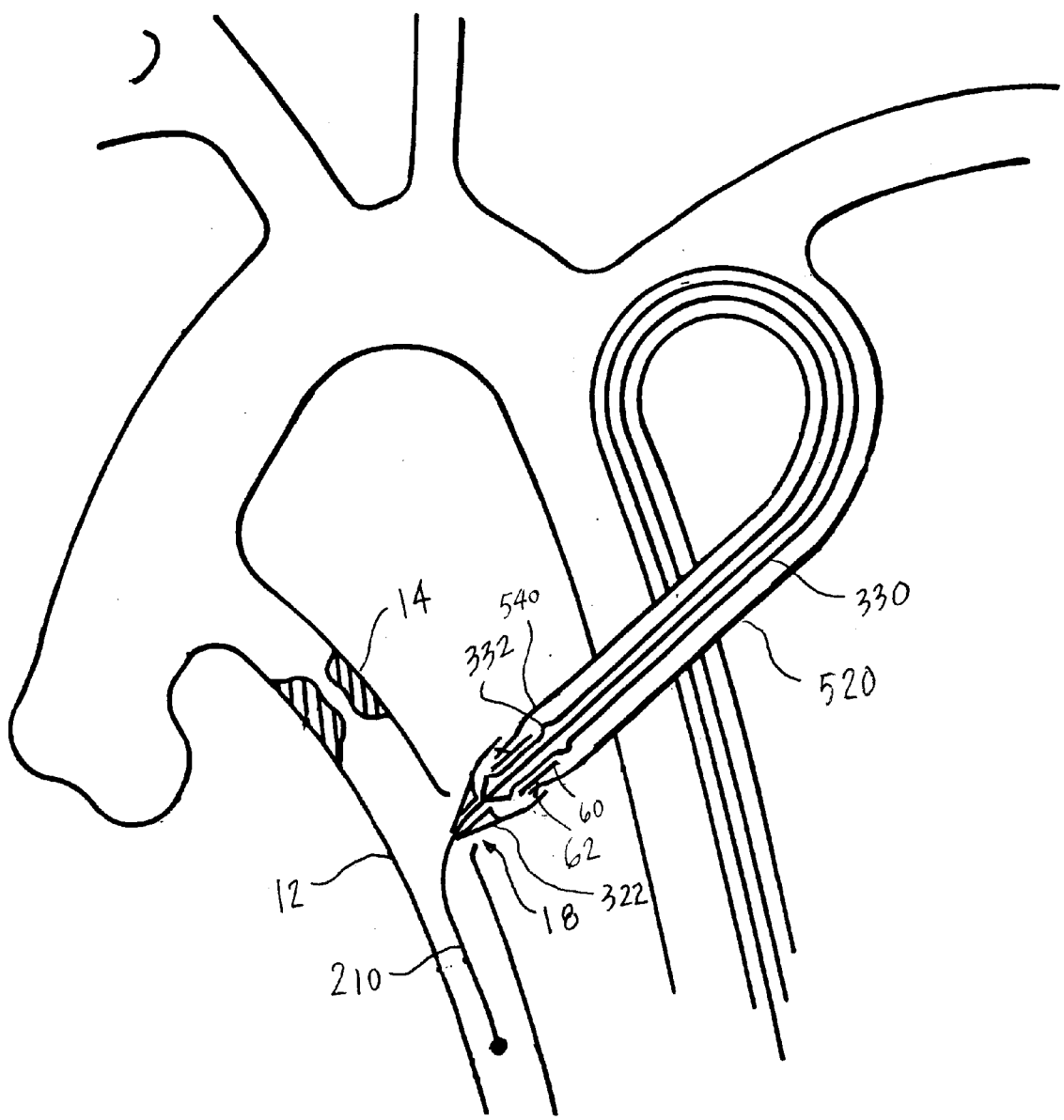
FIG. 45 is a view similar to FIG. 42 showing a later stage in use of illustrative apparatus and methods in accordance with the invention.

Balloon structure 332 and body portion 330 are introduced intraluminally over guide member 210 to the free end portion 540 of the IMA 520, as illustrated in FIG. 45. Introduction cone 322 may be positioned over guide member 210 at the free end portion 540 of the IMA. Cone 322 may be introduced surgically by a small incision in the patient and positioned at the end portion 540. Alternatively, cone 322 may be introduced intraluminally through the patient's circulatory system to the end portion 540 simultaneously with balloon structure 332. Balloon structure 332 engages the inner surface of component 60. (This may be achieved by frictional engagement, such as by advancing balloon structure 332 within component 60 and slightly inflating balloon structure 332). Further advancement of the balloon structure 332 and tube 330 advances component 60 and the IMA 520 therewith. Assistance in moving the end portion of the IMA and the connector to the distal anastomosis location may be additionally provided by surgical apparatus, similar to apparatus 440 (see, FIGS. 42–43), introduced through the surgical access opening. Component 60 is installed in the lumen of the coronary artery 12, substantially as described above with respect to FIGS. 15–17.

Figure 46:
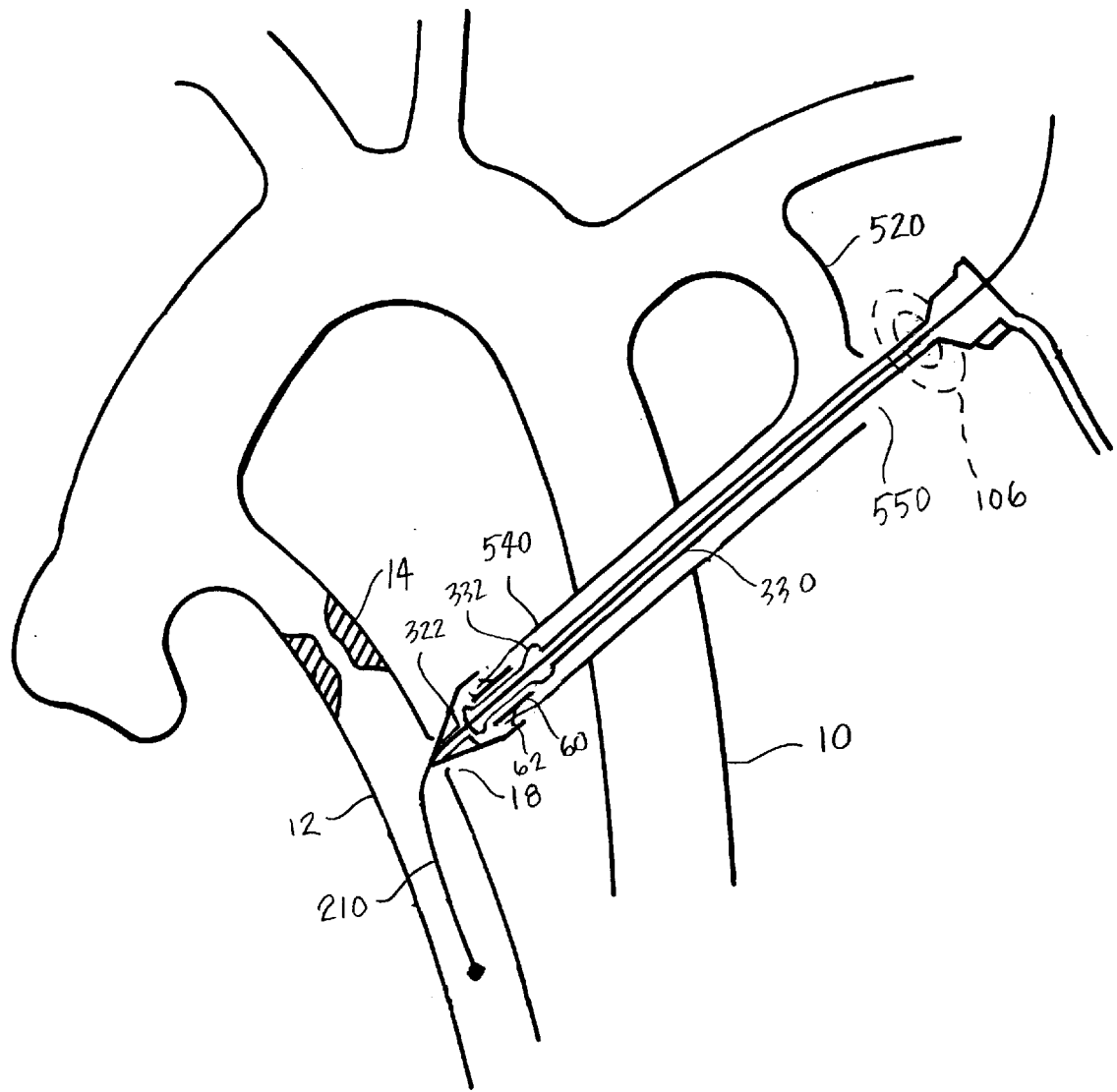
FIG. 46 is a view similar to FIG. 43, illustrating another alternative embodiment in accordance with the invention.

Another alternative embodiment is illustrated in FIG. 46, which is similar to the apparatus and methods described above with respect to FIG. 45. Connector 60 is attached to the end portion 540 of the IMA 520. In order to surgically install the IMA 520 in the coronary artery 12, an arteriotomy 550 is made remote from the severed end portion 540. The delivery apparatus, including balloon structure 332 and tube 330, may be inserted into the patient via an access opening 106, such as an incision or a small cannula, and into arteriotomy 550 and along and through the IMA 520, to the end portion 540 adjacent component 60. Installation of the end portion 540 of the IMA 520 proceeds substantially as described above. After installation is completed, balloon structure 332 and tube 330, introduction cone 322, and guide member 210 are withdrawn. Sutures or other closing means are applied to the IMA at the arteriotomy 550 to complete the procedure.

Although in some embodiments of this invention it is not necessary in accordance to intraluminally approach more than one end of the graft site, it is not inconsistent with this invention to also use other instrumentation to intraluminally approach the other end of the graft site. For example, it may be desirable to introduce a catheter into coronary artery 12 during the procedure described above that includes FIG. 1 and related FIGS. in order to medicate the coronary artery, to introduce radiologic (e.g., fluoroscopic) liquids into the coronary artery, etc.

It will be understood that the foregoing is only illustrative of the principles of the invention, and that various modifications may be made by those skilled in the art without departing from the scope and spirit of the invention. For example, the sequence of some steps in the procedures described may be changed if desired. The manner in which elements and techniques are used for observation of the apparatus inside the patient may vary. For example, radiologic fluids may be injected into the patient through various lumens in the apparatus to help monitor the location of various apparatus in the patient, and/or radiologic markers may be provided anywhere on the apparatus that may be helpful to the physician.

The invention claimed is:

1. A method for installing a tubular graft between first and second spaced locations in a patient's tubular body structure comprising:

piercing a wall of the tubular body structure at the first location with a distal portion of a first elongated structure inserted into and along a lumen of the tubular body structure to the first location;

piercing a wall of the tubular body structure at the second location with a distal portion of a second elongated structure inserted into and along a lumen of the tubular body structure to the second location;

providing a surgical access opening in the patient adjacent one of the first and second locations;

passing an elongated guide member along the lumen of the tubular body structure, through the wall at one of the first and second locations to the other of the first and second locations;

passing the graft along the lumen of the tubular body structure and over the elongated guide member, through the wall at one of the first and second locations to the other of the first and second locations; and attaching axially spaced portions of the graft to the tubular body structure adjacent the first and second locations.

2. The method defined in claim 1, wherein the elongated structure has a sharpened distal configuration, and the step of piercing the wall of the tubular body structure at the first location comprises:

piercing the wall of the tubular body structure at the first location with the sharpened distal configuration.

3. The method defined in claim 2, wherein the distal portion of the first elongated structure has a substantially hollow configuration, and the step of piercing the wall of the tubular body structure at the first location comprises:

extending the distal portion of the first elongated structure out of the tubular body structure at the first location such that a fluid-tight seal is provided between the distal portion of the first elongated structure and the wall of the tubular body structure at the first location.

4. The method defined in claim 3, wherein the step of passing an elongated guide member along the lumen of the tubular body structure, through the wall at one of the first and second locations to the other of the first and second locations comprises:

inserting an end portion of the elongated guide member into the hollow distal portion of the first elongated structure and into and along the interior of the first elongated structure.

5. The method defined in claim 1, wherein said tubular body structure has a primary fluid flow direction, the method further comprising:

after the step of passing the elongated guide member, orienting an end portion of the elongated guide member positioned in the lumen of the tubular body structure adjacent the second location in a downstream orientation substantially aligned with the fluid flow direction.

6. The method defined in claim 5, wherein the end portion of the elongated guide member has an atraumatic configuration and the step of orienting comprises:

withdrawing the elongated guide member from the tubular structure such that the end portion of the elongated guide member remaining in the lumen of the tubular body structure is oriented at least partially transverse to the fluid flow direction; and reinserting the elongated guide member such that the end portion extends in the fluid flow direction.

7. The method defined in claim 5, further comprising:

securing the distal portion of the second elongated structure within the lumen of the tubular body structure.

8. The method defined in claim 1 further comprises:

providing a connector for providing an anastomotic connection between the graft and the tubular body structure; and attaching the connector to an end portion of the graft.

9. The method defined in claim 8, wherein the connector is configured to expand between a deformed configuration and a relaxed, expanded configuration and the step of attaching comprises:

deforming the connector to the deformed configuration;

inserting the connector into the lumen of the tubular body structure at one of the first and second locations; and expanding the connector to the expanded configuration in the lumen.

10. The method defined in claim 9, wherein the step of deforming further comprises:

providing a tubular structure coaxially surrounding the connector and maintaining the connector in the deformed configuration; and at least partially surrounding the connector with the tubular structure.

11. The method defined in claim 10, wherein the step of expanding further comprises:

retracting the tubular structure with respect to the connector to allow the connector to move to the expanded configuration.

12. The method defined in claim 10, wherein the connector comprises a unitary structure disposed annularly about a longitudinal axis and having axially spaced first and second portions, said first portion having a plurality of annularly spaced first members that are deflectable radially out from a remainder of said structure, said second portion having a plurality of annularly spaced second members that are deflectable radially out from a remainder of said structure, and said structure being configured for annular enlargement, wherein the step of expanding comprises:

retracting the tubular structure with respect to the connector to allow the first members and the second members to deflect radially outward.

13. The method defined in claim 8, wherein the connector defines a constant axial length and a cross-section radially expandable between a first diameter sized for insertion through the wall of the tubular body structure at the second location, and a second diameter, the step of attaching axially spaced portions of the graft to the tubular body structure comprises:

after the step of attaching the connector to the end portion of the graft, inserting the connector while in the first diameter through the wall of tubular body structure at the second location; and expanding the connector from the first diameter to the second diameter while maintaining the constant axial length, thereby securing the end portion of the graft coaxially between the connector and the tubular body structure.

14. The method defined in claim 13, wherein the tubular body structure has a primary fluid flow direction, and the step of inserting the connector comprises passing the connector over the elongated guide member such that the connector is at least partially aligned in the fluid flow direction.

15. A method for installing a tubular graft between first and second spaced locations in a patient's tubular body structure comprising:

piercing a wall of the tubular body structure at the first location with a distal portion of a first elongated structure inserted into and along a lumen of the tubular body structure to the first location;

piercing a wall of the tubular body structure at the second location with a distal portion of a second elongated structure inserted into and along a lumen of the tubular body structure to the second location;

providing a surgical access opening in the patient adjacent one of the first and second locations;

passing an elongated guide member along the lumen of the tubular body structure, through the wall at one of the first and second locations to the other of the first and second locations;

passing the graft along the lumen of the tubular body structure and over the elongated guide member, through the wall at one of the first and second locations to the other of the first and second locations;

attaching axially spaced portions of the graft to the tubular body structure adjacent the first and second locations; and wherein the step of passing an elongated guide member along the lumen of the tubular body structure, through the wall at one of the first and second locations to the other of the first and second locations comprises accessing the elongated guide member with instrumentation inserted into the surgical access opening.

16. The method defined in claim 15, wherein the second elongated structure comprises a deflection structure configured to deflect the distal portion of the elongated guide member towards the interior surface of the wall of the tubular body structure and the step of piercing the wall of the tubular body structure at the second location comprises:

deflecting the distal portion of the elongated guide member towards the interior surface of the wall of the tubular body structure; and piercing the wall of the tubular body structure with distal portion of the elongated guide member.

17. A method for installing a tubular graft between first and second spaced locations in a patient's tubular body structure comprising:

piercing a wall of the tubular body structure at the first location with a distal portion of a first elongated structure inserted into and along a lumen of the tubular body structure to the first location;

piercing a wall of the tubular body structure at the second location with a distal portion of a second elongated structure inserted into and along a lumen of the tubular body structure to the second location;

providing a surgical access opening in the patient adjacent one of the first and second locations;

passing an elongated guide member along the lumen of the tubular body structure, through the wall at one of the first and second locations to the other of the first and second locations;

passing the graft along the lumen of the tubular body structure and over the elongated guide member, through the wall at one of the first and second locations to the other of the first and second locations;

attaching axially spaced portions of the graft to the tubular body structure adjacent the first and second locations; and wherein the step of attaching axially spaced portions of the graft to the tubular body structure comprises:

suturing an end portion of the graft to the tubular body structure adjacent one of the first and second locations.

18. The method defined in claim 17, wherein the step of attaching axially spaced portions of the graft to the tubular body structure further comprises:

providing suturing apparatus through the surgical access opening.

* * * * *